(12) United States Patent
Marchionni

(10) Patent No.: US 10,717,775 B2
(45) Date of Patent: Jul. 21, 2020

(54) METHODS FOR CARDIOMYOCYTE SURVIVAL, PROLIFERATION OR DIFFERENTIATION BY NRG-2

(71) Applicant: Acorda Therapeutics, Inc., Ardsley, NY (US)

(72) Inventor: Mark Marchionni, Arlington, MA (US)

(73) Assignee: Acorda Therapeutics, Inc., Ardsley, NY (US)

( * ) Notice: Subject to any disclaimer, the term of this patent is extended or adjusted under 35 U.S.C. 154(b) by 0 days.

(21) Appl. No.: 16/116,271

(22) Filed: Aug. 29, 2018

(65) Prior Publication Data

US 2019/0169248 A1 Jun. 6, 2019

Related U.S. Application Data

(63) Continuation of application No. 14/576,706, filed on Dec. 19, 2014, now Pat. No. 10,065,999, which is a continuation of application No. 13/372,075, filed on Feb. 13, 2012, now abandoned, which is a continuation of application No. 11/085,812, filed on Mar. 21, 2005, now Pat. No. 8,114,838, which is a continuation of application No. 09/864,675, filed on May 23, 2001, now Pat. No. 6,890,751.

(60) Provisional application No. 60/206,495, filed on May 23, 2000.

(51) Int. Cl.

| | | |
|---|---|---|
| *A61K 38/00* | (2006.01) | |
| *A61K 49/00* | (2006.01) | |
| *A61K 38/18* | (2006.01) | |
| *C07K 14/475* | (2006.01) | |
| *C07K 14/48* | (2006.01) | |
| *C07K 14/00* | (2006.01) | |
| *A61K 35/34* | (2015.01) | |
| *A61K 38/16* | (2006.01) | |
| *A61K 45/00* | (2006.01) | |
| *A61K 38/17* | (2006.01) | |
| *A61K 47/42* | (2017.01) | |
| *C07K 14/485* | (2006.01) | |
| *A61P 9/06* | (2006.01) | |
| *A61P 9/00* | (2006.01) | |
| *A61P 9/04* | (2006.01) | |
| *C07K 14/47* | (2006.01) | |
| *C07K 14/71* | (2006.01) | |
| *A61P 9/10* | (2006.01) | |
| *G01N 33/50* | (2006.01) | |
| *G01N 33/68* | (2006.01) | |
| *A61K 39/00* | (2006.01) | |

(52) U.S. Cl.
CPC ...... *C07K 14/4756* (2013.01); *A01K 2217/05* (2013.01); *A61K 35/34* (2013.01); *A61K 38/00* (2013.01); *A61K 38/16* (2013.01); *A61K 38/17* (2013.01); *A61K 38/1709* (2013.01); *A61K 38/18* (2013.01); *A61K 38/1883* (2013.01); *A61K 45/00* (2013.01); *A61K 47/42* (2013.01); *A61K 2039/55516* (2013.01); *A61K 2039/6031* (2013.01); *A61K 2300/00* (2013.01); *A61P 9/00* (2018.01); *A61P 9/04* (2018.01); *A61P 9/06* (2018.01); *A61P 9/10* (2018.01); *C07K 14/00* (2013.01); *C07K 14/47* (2013.01); *C07K 14/475* (2013.01); *C07K 14/485* (2013.01); *C07K 14/71* (2013.01); *C07K 2319/00* (2013.01); *C12N 2830/85* (2013.01); *G01N 33/5061* (2013.01); *G01N 33/68* (2013.01); *G01N 2333/4756* (2013.01); *G01N 2333/485* (2013.01); *G01N 2333/71* (2013.01); *G01N 2500/10* (2013.01); *G01N 2800/32* (2013.01); *G01N 2800/325* (2013.01); *G01N 2800/52* (2013.01)

(58) Field of Classification Search
CPC ............ A61K 2300/00; A61K 38/1883; A61K 38/18; A61K 38/00; A61K 38/1808; A61K 38/16; A61K 38/1709; A61K 38/1825; A61K 35/12; A61K 35/35; A61K 38/17; G01N 2333/4756; G01N 2333/485; G01N 2800/325; G01N 33/5061; G01N 33/5044; C07K 14/485
See application file for complete search history.

(56) References Cited

U.S. PATENT DOCUMENTS

| | | |
|---|---|---|
| 5,530,109 A | 6/1996 | Goodearl et al. |
| 5,716,930 A | 2/1998 | Goodearl et al. |
| 5,912,326 A | 6/1999 | Chang |
| 6,087,323 A | 7/2000 | Gwynne et al. |
| 6,444,642 B1 * | 9/2002 | Sklar ..................... C07K 14/82 514/16.5 |

(Continued)

FOREIGN PATENT DOCUMENTS

| | | |
|---|---|---|
| JP | H11-512285 A | 10/1999 |
| WO | 94/00140 A1 | 1/1994 |

(Continued)

OTHER PUBLICATIONS

Alaoui-Ismaili et al., Cytokine Growth Factor Rev. 2009; 20:501-507.*

(Continued)

*Primary Examiner* — Chang-Yu Wang
(74) *Attorney, Agent, or Firm* — Mintz Levin Cohn Ferris Glovsky and Popeo, P.C.

(57) ABSTRACT

The invention features methods of treatment and diagnosis using NRG-2 polypeptides, nucleic acid molecules, and antibodies. The invention also provides novel NRG-2 polypeptides and nucleic acid molecules.

9 Claims, 12 Drawing Sheets

Specification includes a Sequence Listing.

(56) References Cited

U.S. PATENT DOCUMENTS

| | | | |
|---|---|---|---|
| 6,635,249 B1* | 10/2003 | Marchionni | A61K 39/395 424/145.1 |
| 6,890,751 B2 | 5/2005 | Marchionni | |
| 7,037,888 B1* | 5/2006 | Sklar | A61K 38/1883 514/1.9 |
| 7,115,554 B1* | 10/2006 | Sklar | C07K 14/82 514/1.9 |
| 7,384,756 B1* | 6/2008 | Sklar | C07K 14/82 435/7.2 |
| 7,662,772 B2* | 2/2010 | Marchionni | A61K 39/395 514/1.1 |
| 7,718,606 B2* | 5/2010 | Sklar | C07K 14/82 514/7.6 |
| 7,776,817 B2 | 8/2010 | Ford | |
| 7,968,678 B2* | 6/2011 | Goodearl | C07K 14/4756 530/324 |
| 7,973,007 B2 | 7/2011 | Ford | |
| 8,026,213 B2* | 9/2011 | Sklar | C07K 14/82 514/7.6 |
| 8,076,283 B2* | 12/2011 | Marchionni | A61K 39/395 514/9.6 |
| 8,114,838 B2* | 2/2012 | Marchionni | C07K 14/4756 514/7.6 |
| 8,394,761 B2* | 3/2013 | Marchionni | A61K 39/395 514/7.6 |
| 10,065,999 B2* | 9/2018 | Marchionni | C07K 14/4756 |
| 10,232,016 B2* | 3/2019 | Marchionni | A61K 39/395 |
| 2002/0127716 A1 | 9/2002 | Feron et al. | |
| 2012/0214737 A1 | 8/2012 | Marchionni | |

FOREIGN PATENT DOCUMENTS

| | | | |
|---|---|---|---|
| WO | 94/00149 A1 | | 1/1994 |
| WO | 94/26298 A1 | | 11/1994 |
| WO | 97/09425 A1 | | 3/1997 |
| WO | 98/07736 A1 | | 2/1998 |
| WO | WO00/64400 | * | 11/2000 |
| WO | 02/22685 A2 | | 3/2002 |

OTHER PUBLICATIONS

Guo et al., PNAS 2004; 101:9205-9210.*
Bowie et al. Science, 1990, 247:1306-1310.*
Pawson et al. 2003, Science 300:445-452.*
Jones, FEBS Lett. 1999; 447:227-231.*
Burgess et al. J of Cell Bio. 1990, 111:2129-2138.*
Lopez-Garcia et al. (2004) "Postnatal Neurogenesis and Neuronal Regeneration", Brain Damage and Repair: From Molecular Research to Clinical Therapy. Herdegen et al. (Abstract only).
Ma et al. (Nov. 1999) "Neuregulins signaling via a glial erbB-2-erbB-4 receptor complex contribute to the neuroendocrine control of mammalian sexual development", The Journal of Neuroscience, 19(22):9913-9927.
Marchionni et al. (Mar. 25, 1993) "Glial Growth Factors are Alternatively Spliced ErbB2 Ligands Expressed in the Nervous System", Nature, 362:312-318.
Mathern et al. (2002) "Seizures decrease postnatal neurogenesis and granule cell development in the human fascia dentata", Epilepsia, 43(5):68-73.
McCarthy et al. (1980) "Preparation of separate astroglial and oligodendroglial cell cultures from rat cerebral tissue", Journal of Cell Biology, 85:890-902.
Meyer et al. (Feb. 1994) "Distinct Isoforms of Neuregulin are Expressed in Mesenchymal and Neuronal Cells During Mouse Development", PNAS, 91:1064-1068.
Meyer et al. (1997) "Isoform-Specific Expression and Function of Neuregulin", Development, 124:3575-3586.
Meyer et al. (Dec. 14, 1995) "Multiple Essential Functions of Neuregulin in Development", Nature, 378:386-390.
Nagata et al. (Aug. 1, 1994) "Solution Structure of the Epidermal Growth Factor-Like Domain of Heregulin-α, a Ligand for p180erbB-4", The EMBO Journal, 13(15):3517-3523.
Orr-Urtreger et al. (Mar. 1993) "Neural Expression and Chromosomal Mapping of Neu Differentiation Factor to 8p12-p21", PNAS, 90(5):1867-1871.
Ozcelik et al. (Jun. 25, 2002) "Conditional Mutation of the ErbB2 (HER2) Receptor in Cardiomyocytes Leads to Dilated Cardiomyopathy", PNAS, 99(13):8880-8885.
Peles et al. (Apr. 3, 1992) "Isolation of the NeuHER-2 Stimulatory Ligand: A 44 kd Glycoprotein that Induces Differentiation of Mammary Tumor Cells", Cell, 69(1):205-216.
Peles et al. (Dec. 1993) "Neu and its ligands: From an Oncogene to Neural Factors", Bioessays, 15(12):815-824.
Pinkas-Kramarski et al. (Sep. 1994) "Brain Neurons and Glial Cells Express Neu Differentiation Factor/Heregulin: A Survival Factor for Astrocytes", PNAS, 91:9387-9391.
Pinkas-Kramarski et al. (1997) "Differential Expression of NDF/Neuregulin Receptors Erbb-3 and Erbb-4 and Involvement in Inhibition of Neuronal Differentiation", Oncogene, 15:2803-2815.
Pinkas-Kramarski et al. (1996) "Diversification of Neu Differentiation Factor and Epidermal Growth Factor Signaling by Combinatorial Receptor Interactions", The EMBO Journal, 15:2452-2467.
Pinkas-Kramarski et al. (Oct. 1998) "ErbB Tyrosine Kinases and the Two Neuregulin Families Constitute a Ligand-Receptor Network", Molecular and Cellular Biology, 18(10):6090-6101.
Pollock et al. (Mar. 1999) "Neuregulin is a mitogen and survival factor for olfactory bulb ensheathing cells and an isoform is produced by astrocytes", European Journal of Neuroscience 11(3):769-780.
Porter et al. (Oct. 1, 1986) "Schwann cells stimulated to proliferate in the absence of neurons retain full frunctional capability", Journal of Neuroscience, 6(10):3070-3078.
Ram et al. (2000) "Heregulin-beta is especially potent in activating phosphatidylinositol 3-kinase in nontransformed human mammary epithelial cells", Journal of Cellular Physiology, 183(3):301-313.
Ring et al. (May 1999) "The human neuregulin-2 (NRG2) gene: cloning, mapping and evaluation as a candidate for the autosomal recessive form of Charcot-Marie-Tooth disease linked to 5q", Human Genetics, 104(4):326-332.
Rio et al. (Jul. 1997) "Neuregulin and erbB Receptors Play a Critical Role in Neuronal Migration", Neuron, 19(1):39-50.
Sawyer et al. (Jun. 2011) "Neuregulin-1β for the Treatment of Systolic Heart Failure", Journal of Molecular and Cellular Cardiology, 51(4):501-505.
Sommer et al. (1981) "Monoclonal antibodies (O1 to O4) to oligodendrocyte cell surfaces: an immunocytological study in the central nervous system", Developmental Biology, 83:311-327.
Springhorn et al. (Jul. 15, 1992) "Transcriptional Regulation in Cardiac Muscle", Journal of Biological Chemistry, 267(20):14360-14365.
Stewart et al. (Jun. 2001) "More 'malignant' than Cancer? Five-year Survival Following a First Admission for Heart Failure", European Journal of Heart Failure, 3(3):315-322.
Sutherland et al. (2012) "Neuroprotection for Ischaemic Stroke: Translation from the Bench to the Bedside", International Journal of Stroke, 7(5):407-418.
T Hart et al. (2003) "The Use of Animal Models to Investigate the Pathogenesis of Neuroinflammatory Disorders of the Central Nervous System", Current Opinion in Neurology, 16:375-383.
Vartanian et al. (Nov. 1994) "A role for the acetylcholine receptor-inducing protein ARIA in oligodendrocyte development", PNAS, 91(24):11626-11630.
Von Bohlen Und Halbach (Sep. 2007) "Immunohistological markers for staging neurogenesis in adult hippocampus", Cell and Tissue Research, 329(3):409-420.
Wen et al. (May 1, 1992) "Neu Differentiation Factor: A Transmembrane Glycoprotein Containing an EGF Domain and an Immunoglobulin Homology Unit.", Cell, 69(3):559-572.
Wikipedia (Jan. 23, 2007) "Glial cell", retrieved from https://simple.wikipedia.org/wiki/Glial_cell, 01 page.

(56) References Cited

OTHER PUBLICATIONS

Xu et al. (2008) "Extended Therapeutic Window and Functional Recovery after Intraarterial Administration of Neuregulin-1 after Focal Ischemic Stroke", Journal of Cerebral Blood Flow & Metabolism, 28(9):527-535.
Yamada et al. (Sep. 5, 2000) "Characterization of the human NTAK gene structure and distribution of the isoforms for rat NTAK mRNA", Gene. 255(1):15-24.
Yang et al. (Feb., 1998) "A cysteine-rich isoform of neuregulin controls the level of expression of neuronal nicotinic receptor channels during synaptogenesis", Neuron, 20(2):255-270.
Yap et al. (1991) "Slide PCR: DNA amplification from cell samples on microscopic glass slides.", Nucleic Acids Research, 19(15):4294.
Zhang et al. (Sep. 1997) "Neuregulin-3 (NRG3): A Novel Neural Tissue-Enriched Protein That Binds and Activates ErbB4", PNAS, 94(18):9562-9567.
Zhao et al. (Apr. 24, 1998) "Neuregulins Promote Survival and Growth of Cardiac Myocytes", Journal of Biological Chemistry, 273(17):10261-10269.
Jones et al. "Binding Specificities and Affinities of egf Domains for ErbB Receptors." FEBS Lett. 447.2-3(1999): 227-231.
European Search Report for Application No. 10180489, dated Jul. 7, 2011.
Israeli Office Action for Application No. 153052, dated Nov. 22, 2010.
Japanese Office Action for Application No. 2001-585810, dated Feb. 9, 2011.
(2000) "American Heritage Dictionary", Houghton Mifflin Company.
Ackman et al. (2007) "Citron kinase is required for postnatal neurogenesis in the hippocampus", International Journal of Developmental Neuroscience, 29(1-2):113-123.
Adlkofer et al. (2000) "Role of neuregulins in glial cell development", Glia, 29:104-111.
Anton et al. (1997) "Role of GGF/neuregulin signaling in interactions between migrating neurons and radial glia in the developing cerebral cortex", Development, 124(18):3501-3510.
Anton et al. (1996) "Role of neuron-glial junctional domain proteins in the maintenance and termination of neuronal migration across the embryonic cerebral wall", Journal of Neuroscience, 16:2283-2293.
Baek et al. (1998) "Proliferation of human Schwann cells induced by neu differentiation factor isoforms", International Journal of Developmental Neuroscience, 20(6):512-517 (Abstract Only).
Barnett et al. (1993) "Culture of Specific Cell Types", Culture of Animal Cells. Freshney, ed. New York: Wiley-Liss, 337-341.
Barnett et al. (1993) "Purification of olfactory nerve ensheathing cells from the olfactory bulb", Developmental Biology, 155(2):337-350.
Berger et al. (1994) "Continual Electric Field Stimulation Preserves Contractile Function of Adult Ventricular Myocytes in Primary Culture", American Journal of Physiology, 266:H341-H349.
Bermingham-McDonagh et al. (1997) "Neuregulin expression in PNS neurons: isoforms and regulation by target interactions", Molecular and Cellular Neuroscience, 10(3-4):184-195.
Bian et al. (2009) "Neuregulin-1 Attenuated Doxorubicin-Induced Decrease in Cardiac Troponins", American Journal of Physiology-Heart and Circulatory Physiology, 297(6):H1974-H1983.
Bublil et al. (2007) "The EGF Receptor Family: Spearheading a Merger of Signaling and Therapeutics", Current Opinion in Cell Biology, 19(2):124-134.
Buonanno et al. (2001) "Neuregulin and Erbb Receptor Signaling Pathways in the Nervous Sytem", Current Opinion in Neurobiology, 11(3):287-296.
Burden et al. (1997) "Neuregulins and Their Receptors: Meeting Report A Versatile Signaling Module in Organogenesis and Oncogenesis", Neuron, 18(6):847-855.
Busfield et al. (Jul. 1997) "Characterization of a Neuregulin-Related Gene, Don-1, that is Highly Expressed in Restricted Regions of the Cerebellum and Hippocampus", Molecular and Cellular Biology, 17(7):4007-4014.

Canoll et al. (1996) "GGF/Neuregulin is a Neuronal Signal That Promotes the Proliferation and Survival and Inhibits the Differentiation of Oligodendrocyte Progenitors", Neuron, 17(2):229-243.
Carraway et al. (May 29, 1997) "Neuregulin-2, a New Ligand of Erbb3/Erbb4-Receptor Tyrosine Kinases", Nature, 387(6632):512-516.
Carraway et al. (1995) "Neuregulins and Their Receptors", Current Opinion in Neurobiology, 5:606-612.
Chang et al. (May 29, 1997) "Ligands for ErbB-Family Receptors Encoded by a Neuregulin-Like Gene", Nature, 387(6632):509-512.
Chen et al. (Nov. 15, 1994) "Expression of Multiple Neuregulin Transcripts in Postnatal Rat Brains", The Journal of Comparative Neurology, 349(3):389-400.
Cohen et al. (Apr. 1992) "Expression of the neu proto-oncogene by Schwann cells during peripheral nerve development and Wallerian degeneration", Journal of Neuroscience Research, 31(4):622-634.
Corfas et al. (Jan. 1995) "Differential Expression of ARIA Isoforms in the Rat Brain", Neuron, 14:103-115.
Database Uniprot (Dec. 15, 1998) "Proneuregulin-2 precursor (Pro-NRG2)", EBI Accession No. UniProt: 014511, XP-002323733.
Ellingsen et al. (1993) "Adult Rat Ventricular Myocytes Cultured in Defined Medium: Phenotype and Electromechanical Function", American Journal of Physiology, 265:H747-H754.
Evans et al. (Feb. 2002) "Characterization of mitotic neurons derived from adult rat hypothalamus and brain stem", Journal of Neurophysiology, 87(2):1076-1085.
Falls et al. (Mar. 12, 1993) "ARIA, a Protein that Stimulates Acetylcholine Receptor Synthesis, is a Member of the Neu Ligand Family", Cell, 72(5):801-815.
Falls (2003) "Neuregulins: Functions, Forms, and Signaling Strategies", Experimental Cell Research, 284(1):14-30.
Fischbach et al. (1997) "ARIA: a neuromuscular junction neuregulin", Annual Review of Neuroscience, 20:429-458.
Fukazawa et al. (2003) "Neuregulin-1 Protects Ventricular Myocytes From Anthracycline-Induced Apoptosis Via Erbb4-Dependent Activation of PI3-Kinase/AKt", Journal of Molecular and Cellular Cardiology, 35(12):1473-1479.
Gallo et al. (Jan. 1, 1995) "Developmental and growth factor-induced regulation of nestin in oligodendrocyte lineage cells", Journal of Neuroscience, 15(1):394-406.
Gassmann et al. (Nov. 1995) "Aberrant Neural and Cardiac Development in Mice Lacking the ErbB4 Neuregulin Receptor", Nature, 378(6555):390-394.
Gassmann et al. (1997) "Neuregulins and Neuregulin Receptors in Neural Development", Current Opinion in Neurobiology, 7(1):87-92.
Genbank Database (Nov. 14, 1997) "*Homo sapiens* mRNA for NTAK, Complete Cds", Genbank Accession No. AB005060.1, 2 pages.
Ghashghaei et al. (Feb., 2006) "The role of neuregulin-ErbB4 interactions on the proliferation and organization of cells in the subventricular zone", PNAS, 103(6):1930-1935.
Higashiyama et al. (1997) "A Novel Brain-Derived Member of the Epidermal Growth Factor Family That Interacts with ErbB3 and ErbB4", Journal of Biochemistry, 122(3):675-680.
Hijazi et al. (1998) "NRG-3 in Human Breast Cancers: Activation of Multiple ErbB Family Proteins", International Journal of Oncology, 13(5):1061-1067.
Ho et al. (1995) "Sensory and motor neuron-derived factor. A novel heregulin variant highly expressed in sensory and motor neurons", Journal of Biological Chemistry, 270(24):14523-14532.
Hobbs et al. (Dec. 2002) "Neuregulin isoforms exhibit distinct patterns of ErbB family receptor activation", Oncogene, 21(55):8442-8452.
Holmes et al. (May 22, 1992) "Identification of Heregulin, a Specific Activator of p185erbB2", Science, 256(5060):1205-1210.
Hynes et al. (Apr. 2009) "ErbB Receptors and Signaling Pathways in Cancer", Current Opinion in Cell Biology, 21(2):177-184.
Iaci et al. (Dec. 2010) "Glial Growth Factor 2 Promotes Functional Recovery with Treatment Initiated up to 7 days after Permanent Focal Ischemic Stroke", Neuropharmacology, 59(7-8):640-649.

(56) References Cited

OTHER PUBLICATIONS

Iacopetti et al. (Apr. 1999) "Expression of the antiproliferative gene TIS21 at the onset of neurogenesis identifies single neuroepithelial cells that switch from proliferative to neuron-generating division", PNAS, 96(8):4639-4644.
Karunagaran et al. (1996) "ErbB-2 is a common auxiliary subunit of NDF and EGF receptors: implications for breast cancer", The EMBO Journal, 15:254-264.
Kastin et al. (Feb. 2004) "Neuregulin-1-β1 Enters Brain and Spinal Cord by Receptor-Mediated Transport", Journal of Neurochemistry, 88(4):965-970.
Lai et al. (May 1991) "An Extended Family of Protein-Tyrosine Kinase Genes Differentially Expressed in the Vertebrate Nervous System", Neuron, 6(5):691-704.
Lee et al. (1995) "Requirement for neuregulin receptor erbB2 in neural and cardiac development", Nature, 378(6555):394-398.
Lemke (1996) "Neuregulins in Development", Molecular and Cellular Neuroscience, 7:247-262.
Levi (Feb. 1995) "The influence of heregulins on human Schwann cell proliferation", The Journal of Neuroscience, 15(2):1329-1340.
Li et al. (Dec. 15, 1998) "Regeneration of adult rat corticospinal axons induced by transplanted olfactory ensheathing cells", Journal of Neuroscience, 18(24):10514-10524.
Liu et al. (Oct. 3, 2006) "Neuregulin-1/erbB-Activation Improves Cardiac Function and Survival in Models of Ischemic, Dilated, and Viral Cardiomyopathy", Journal of the American College of Cardiology, 48(7):1438-1447.

\* cited by examiner

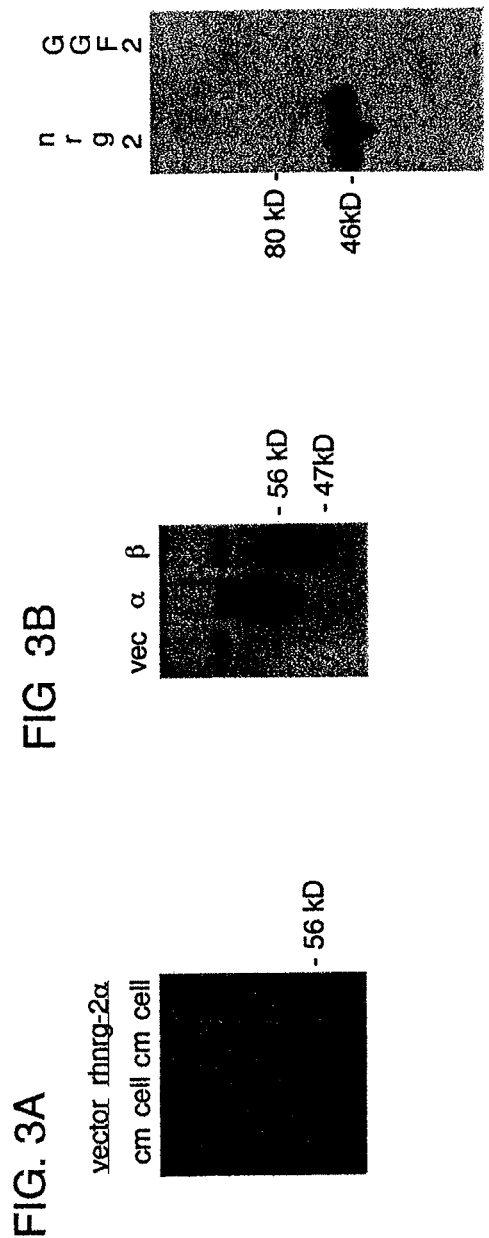

NRG2B

From the Scan of this Lane the NRG2B is 92.5% Pure

Approximate Molecular Weight (kd)

FIG. 11A
FIG. 11B
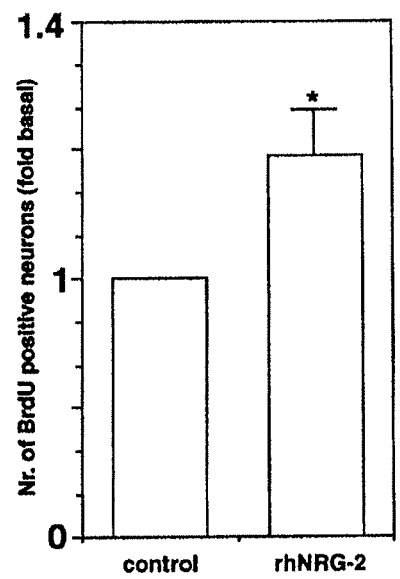

METHODS FOR CARDIOMYOCYTE SURVIVAL, PROLIFERATION OR DIFFERENTIATION BY NRG-2

RELATED APPLICATIONS

This patent application is a continuation of U.S. patent application Ser. No. 14/576,706, filed Dec. 19, 2014 (now U.S. Pat. No. 10,065,999, issued on Sep. 4, 2018), which is continuation application of U.S. patent application Ser. No. 13/372,075 (abandoned), filed Feb. 13, 2012, which is a continuation application of U.S. patent application Ser. No. 11/085,812, filed Mar. 21, 2005 (now U.S. Pat. No. 8,114,838, issued on Feb. 14, 2012), which is a continuation application of U.S. patent application Ser. No. 09/864,675, filed May 23, 2001 (now U.S. Pat. No. 6,890,751, issued on May 10, 2005), which claims the benefit of and priority to U.S. Patent Application Ser. No. 60/206,495, filed May 23, 2000, each of which is hereby incorporated by reference in its entirety.

FIELD OF THE INVENTION

The invention relates to neuregulins and methods for their use.

INCORPORATION OF SEQUENCE LISTING

The contents of the text file named "043509-509C04US ST25.txt", which was created on Feb. 14, 2019 and is 10.9 KB in size, are hereby incorporated by reference in their entirety.

BACKGROUND OF THE INVENTION

Neuregulins (NRGs) and their receptors constitute a growth factor-receptor tyrosine kinase system for cell-cell signalling that has been implicated in organogenesis in nerve, muscle, epithelia, and other tissues (Lemke, *Mol. Cell. Neurosci.* 7: 247-262, 1996; Burden et al., *Neuron* 18: 847-855, 1997). The three known NRG genes, NRG-1, NRG-2, and NRG-3, map to distinct chromosomal loci (Pinkas-Kramarski et al., *Proc. Natl. Acad. Sci. USA* 91: 9387-91, 1994; Carraway et al., *Nature* 387: 512-516, 1997; Chang et al., *Nature* 387:509-512, 1997; and Zhang et al., *Proc. Natl. Acad. Sci. USA* 94: 9562-9567, 1997), and collectively encode a diverse array of NRG proteins. The NRG protein family includes at least 20 (and perhaps 50 or more) secreted and membrane-bound isoforms containing epidermal growth factor-like (EGFL), immunoglobulin (Ig), and other recognizable domains.

The most thoroughly studied NRG proteins to date are the gene products of NRG-1, which include a group of approximately 15 distinct structurally-related isoforms (Lemke, *Mol. Cell. Neurosci.* 7: 247-262, 1996 and Peles and Yarden, *BioEssays* 15: 815-824, 1993). Isoforms of NRG-1 include Neu Differentiation Factor (NDF; Peles et al., *Cell* 69, 205-216, 1992 and Wen et al., *Cell* 69, 559-572, 1992), Heregulin (HRG; Holmes et al., *Science* 256: 1205-1210, 1992), Acetylcholine Receptor Inducing Activity (ARIA; Falls et al., *Cell* 72: 801-815, 1993), and the glial growth factors GGF1, GGF2, and GGF3 (Marchionni et al., *Nature* 362: 312-8, 1993).

The NRG-2 gene was identified by homology cloning (Chang et al., *Nature* 387:509-512, 1997; Carraway et al., *Nature* 387:512-516, 1997; and Higashiyama et al., 0.1 *Biochem.* 122: 675-680, 1997) and through genomic approaches (Busfield et al., *Mol. Cell. Biol.* 17:4007-4014, 1997). NRG-2 isoforms include Neural-and Thymus-Derived Activator of erbB Kinases (NTAK; Genbank Accession No. AB005060), Divergent of Neuregulin (Don-1), and Cerebellum-Derived Growth Factor (CDGF; PCT application WO 97/09425). Cells expressing erbB4 or erbB2/erbB4 receptors may show a particularly robust response to NRG-2 (Pinkas-Kramarski et al., *Mol. Cell. Biol.* 18: 6090-6101, 1998). The NRG-3 gene product (Zhang et al., *Proc. Natl. Acad. Sci. USA* 94: 9562-9567, 1997) is also known to bind and activate erbB4 receptors (Hijazi et al., *Int. J. Oncol.* 13:1061-1067, 1998).

The EGFL domain, present at the core of NRG isoforms, is required for binding and activating NRG receptors, which belong to the epidermal growth factor receptor (EGFR) family, and include EGFR (or erbB1), erbB2, erbB3, and erbB4, also known as HER1 through HER4, respectively, in humans (Meyer et al., *Development* 124: 3575-3586, 1997; Orr-Urtreger et al., *Proc. Natl. Acad. Sci. USA* 90: 1867-71, 1993; Marchionni et al., *Nature* 362: 312-8, 1993; Chen et al., *J. Comp. Neurol.* 349: 389-400, 1994; Corfas et al., *Neuron* 14: 103-115, 1995; Meyer et al., *Proc. Natl. Acad. Sci. USA* 91:1064-1068, 1994; and Pinkas-Kramarski et al., *Oncogene* 15: 2803-2815, 1997). High-affinity binding of the NRGs may be mediated principally via either the erbB3 or erbB4 receptors. Binding of NRG ligands leads to dimerization with other erbB subunits and transactivation by phosphorylation on specific tyrosine residues.

NRG proteins have diverse biological properties, making them potentially useful in the development of novel therapies for a wide range of diseases and disorders.

SUMMARY OF THE INVENTION

The invention provides methods of treatment and diagnosis using NRG-2 polypeptides, nucleic acid molecules, and antibodies. The invention also provides novel NRG-2 polypeptides and nucleic acid molecules.

In the first aspect, the invention provides a method for increasing the mitogenesis, survival, growth, or differentiation of a cell by administering a NRG-2 polypeptide to the cell in an amount effective for increasing the mitogenesis, survival, growth, or differentiation of the cell, where the cell expresses an erbB receptor that is selective for a NRG-2 polypeptide. In preferred embodiments of this aspect, the erbB receptor is an erbB4 homodimer, an erbB2/erbB4 heterodimer, or an erbB1/erbB3 heterodimer. In other preferred embodiments of the first aspect, the cell is a neuronal cell, a neuronal progenitor cell, a neuronal-associated cell, or a muscle cell. In other preferred embodiments of the first aspect, the neuronal-associated cell is a Schwann cell, an astrocyte, an oligodendrocyte, an O-2A progenitor cell, a glial cell, a microglial cell, an olfactory bulb ensheathing cell, or a sensory organ cell, and the muscle cell is a myoblast, a satellite cell, a myocyte, a skeletal muscle cell, a smooth muscle cell, or a cardiac muscle cell.

In a second aspect, the invention provides a method of stimulating mitogenesis of a glial cell by contacting the glial cell with a recombinant NRG-2 polypeptide. In a preferred embodiment of the second aspect, the glial cell is an oligodendrocyte, a microglial cell, a myelinating glial cell, an olfactory bulb ensheathing cell, or a glial cell in an adult.

In a third aspect, the invention provides a method for inducing myelination of a neuronal cell by a glial cell by contacting the glial cell with a NRG-2 polypeptide, such that the contacting is sufficient to induce myelination of the neuronal cell by the glial cell.

In a fourth aspect, the invention provides a method of increasing the cardiomyocyte survival, cardiomyocyte proliferation, cardiomyocyte growth, or cardiomyocyte differentiation, in a mammal in need thereof, by administering a NRG-2 polypeptide to the mammal in an amount effective for increasing the cardiomyocyte survival, cardiomyocyte proliferation, cardiomyocyte growth, or cardiomyocyte differentiation. In preferred embodiments of the fourth aspect, the mammal is a human. In other preferred embodiments of the fourth aspect, the mammal has a pathophysiological condition that affects cardiac muscle, for example, cardiomyopathy (e.g., a degenerative congenital disease), cardiac trauma, heart failure, or ischemic damage, or the mammal has a pathophysiological condition that affects smooth muscle, for example, atherosclerosis, vascular lesion, vascular hypertension, or degenerative congenital vascular disease. In another preferred embodiment of the fourth aspect the mammal is a patient with myasthenia gravis.

In a fifth aspect, the invention provides a method of affecting cellular communication between a neuronal-associated cell and a neuronal cell in a mammal by administering a NRG-2 polypeptide to the mammal, such that the neuregulin interacts with the neuronal-associated cell, resulting in the production of at least one neurotrophic agent by the neuronal-associated cell, and the neurotrophic agent or agents affect the mitogenesis, survival, growth, differentiation, or neurite outgrowth of the neuronal cell. In a preferred embodiment of the fifth aspect, the mammal is a human. In other preferred embodiments of the first aspect, the neuronal-associated cell is a Schwann cell, an astrocyte, an oligodendrocyte, an O-2A progenitor cell, a glial cell, an olfactory bulb ensheathing cell, a microglial cell, a sensory organ cell, or a muscle cell (e.g., a skeletal muscle cell, a smooth muscle cell, or a cardiac muscle cell). In other preferred embodiments of the fifth aspect, the cellular communication is affected in the central nervous system or the peripheral nervous system of a mammal. In other preferred embodiments of the fifth aspect, the administering includes administering a purified NRG-2 polypeptide-producing cell.

In a sixth aspect, the invention provides a method for the treatment or prophylaxis of a pathophysiological condition of the nervous system in a mammal, by administering a therapeutically-effective amount of a recombinant NRG-2 polypeptide to the mammal. In preferred embodiments of the sixth aspect, the pathophysiological condition is a condition of the peripheral nervous system or the central nervous system; the pathophysiological condition is demyelination of nerve cells, damage of Schwann cells, loss of Schwann cells, or a neurodegenerative disorder; the pathophysiological condition is a peripheral neuropathy (e.g., a sensory nerve fiber neuropathy, a motor fiber neuropathy, or both); or the pathophysiological condition is multiple sclerosis, amyotrophic lateral sclerosis, spinal muscular atrophy, nerve injury, Alzheimer's Disease, Parkinson's Disease, cerebellar ataxia, or spinal cord injury. In another preferred embodiment of the sixth aspect, the treatment or prophylaxis requires neural regeneration or neural repair. In another preferred embodiment of the sixth aspect, the NRG-2 polypeptide interacts with neuronal-associated cells, resulting in production of at least one neurotrophic agent by the neuronal-associated cells, and the neurotrophic agent or agents affect the mitotic activity, survival, differentiation or neurite outgrowth of neuronal cells. In another preferred embodiment of the sixth aspect, the administering is sufficient to induce myelination of a neuronal cell by a glial cell (e.g., a Schwann cell or an oligodendrocyte). In another preferred embodiment of the sixth aspect, the administering includes administering a purified NRG-2 polypeptide-producing cell to the mammal. The NRG-2 polypeptide-producing cell of the invention may contain a recombinant DNA sequence, where the DNA sequence includes a NRG-2 polypeptide-encoding sequence, and where the NRG-2 polypeptide-encoding DNA sequence is operably-linked to a promoter.

In a seventh aspect, the invention provides a method for the treatment of a tumor (e.g., a glial tumor) by inhibiting the proliferation of a tumor cell by administering an effective amount of an antibody, that inhibits binding of a NRG-2 polypeptide to a receptor present on the surface of the tumor cell, to a subject in need of such treatment. In a preferred embodiment of the seventh aspect, the tumor cell expresses an erbB receptor that is selective for a NRG-2 polypeptide.

In an eighth aspect, the invention provides a method for the treatment of neurofibromatosis by inhibiting glial cell mitogenesis by administering an effective amount of an antibody, that inhibits binding of a NRG-2 polypeptide to a receptor present on the surface of a glial tumor cell in an individual with neurofibromatosis, to a subject in need of such treatment.

In a ninth aspect, the invention provides a method for inhibiting proliferation of a cell by contacting the cell with an effective amount of an antibody that inhibits binding of a NRG-2 polypeptide to a receptor present on the surface of the cell.

In a tenth aspect, the invention provides a method for stimulating proliferation of a cell by administering a NRG-2 polypeptide to the cell.

In preferred embodiments of the ninth and tenth aspects, the cell is a neuronal cell, a neuronal-associated cell, or a muscle cell.

The NRG-2 polypeptide of any of the above aspects or embodiments of the invention may include, or consist of, the amino acid sequences set forth in SEQ ID NOs: 2 or 4, or be encoded by the nucleic acid sequences set forth in SEQ ID NOs: 1 or 3.

In an eleventh and a twelfth aspect, the invention provides a substantially pure NRG-2 polypeptide including, or consisting of, the amino acid sequences set forth in SEQ ID NOs: 2 or 4. In a thirteenth aspect, the invention provides a substantially pure nucleic acid molecule including a sequence encoding a polypeptide including the amino acid sequences set forth in SEQ ID NOs: 2 or 4. In preferred embodiments, the invention provides a vector (e.g., a gene therapy vector) including the nucleic acid molecule of the thirteenth aspect, operably linked to a promoter; a cell containing a gene therapy vector that contains the nucleic acid molecule of the thirteenth aspect; and a non-human transgenic animal containing the nucleic acid molecule of the thirteenth aspect.

In fourteenth and fifteenth aspects, the invention provides a substantially pure nucleic acid molecule including, or consisting of, a nucleic acid sequence that is substantially identical to the nucleic acid sequences set forth in SEQ ID NOs: 1 or 3. In a sixteenth aspect, the invention provides a nucleic acid molecule including a sequence that is antisense to the coding strand sequence of the nucleic acid sequence set forth in SEQ ID NOs: 1 or 3, or a fragment thereof.

In a seventeenth aspect, the invention provides a non-human animal having a knockout mutation in one or both alleles encoding the NRG-2 polypeptide including the amino acid sequence set forth in SEQ ID NOs: 2 or 4. In a preferred embodiment of the seventeenth aspect, the invention provides a cell from the non-human animal of the seventeenth aspect.

In an eighteenth aspect, the invention provides an antibody that specifically binds to a NRG-2 polypeptide that includes the amino acid sequences set forth in SEQ ID NOs: 2 or 4. In a preferred embodiment of the eighteenth aspect, the invention provides a method of detecting the presence of a NRG-2 polypeptide in a sample by contacting the sample with the antibody of the eighteenth aspect, and assaying for binding of the antibody to the polypeptide. In a preferred embodiment of the eighteenth aspect, the invention provides a kit for the analysis of a NRG-2 polypeptide of a test subject, where the kit includes the antibody of the eighteenth aspect.

In a nineteenth aspect, the invention provides a method of diagnosing an increased likelihood of developing a NRG-2-related disease or condition in a test subject (e.g., a human) by analyzing nucleic acid molecules of the test subject, to determine whether the test subject contains a mutation in NRG-2 gene that encodes a NRG-2 polypeptide including the amino acid sequence set forth in SEQ ID NOs: 2 or 4, where the presence of the mutation is an indication that the test subject has an increased likelihood of developing a NRG-2-related disease. By "neuregulin" or "NRG" is meant a polypeptide that is encoded by a NRG-1, NRG-2, or NRG-3 gene or nucleic acid molecule (e.g., a cDNA), and binds to and activates an erbB receptor or combinations thereof. Generally, a neuregulin possesses recognizable domains, such as an epidermal growth factor-like (EGFL) domain, that binds to and activates an erbB receptor or combinations thereof, and an immunoglobulin (Ig) domain. An EGFL domain bears structural similarity to the EGF receptor-binding domain as disclosed in Holmes et al. (*Science* 256:1205-1210, 1992), U.S. Pat. Nos. 5,530,109, 5,716,930, U.S. Ser. No. 08/461,097, Hijazi et al. (*Int. J. Oncol.* 13:1061-1067, 1998), Chang et al. (*Nature* 387:509-512, 1997), Carraway et al. (*Nature* 87:512-516, 1997), Higashiyama et al. (*J. Biochem.* 122: 675-680, 1997), and PCT publication WO 97/09425.

By "neuregulin 2" or "NRG-2" is meant a polypeptide encoded by a NRG-2 gene, or a NRG-2 nucleic acid molecule, and is described in the specification herein, and in, for example, Carraway et al., *Nature* 387: 512-516, 1997; Chang et al., *Nature* 387: 509-511, 1997; Higashiyama et al., *J. Biochem.* 122: 675-680, 1997; and Busfield et al., *Mol. Cell. Biol.* 17:4007-4014, 1997. NRG-2 isoforms include Neural-and Thymus-Derived Activator of ErbB Kinases (NTAK; Genbank Accession No. AB005060; Higashiyama et al., *J. Biochem.* 122: 675-680, 1997), Divergent of Neuregulin (don-1; PCT publication WO 98/07736), and Cerebellum-Derived Growth Factor (CDGF; PCT publication WO 97/09425; U.S. Pat. No. 5,912,326), incorporated by reference herein, and the NRG-2 molecules described herein. Generally, the erbB1 receptor (EGFR) is a preferred dimerization partner for a NRG-2 polypeptide. Preferred receptor combinations for NRG-2 polypeptides are erbB4 homodimers, erbB2/erbB4 heterodimers, or erbB1/erbB3 heterodimers. A CDGF, don-1, or NTAK polypeptide or nucleic acid molecule, as set forth in the amino acid and nucleic acid sequences disclosed in Higashiyama et al., *J. Biochem.* 122: 675-680, 1997, WO 98/07736, WO 97/09425, and U.S. Pat. No. 5,912,326, may be specifically excluded from certain aspects of the invention. For example, one or more of a CDGF, don-1, or NTAK polypeptide or nucleic acid molecule, may be excluded from the methods for increasing the mitogenesis, survival, growth, or differentiation of a cell; for increasing the cardiomyocyte survival, cardiomyocyte proliferation, cardiomyocyte hypertrophy, or cardiomyocyte differentiation in a mammal; for affecting cellular communication between a neuronal-associated cell and a neuronal cell; for stimulating mitogenesis of a glial cell; for inducing myelination of a neuronal cell by a glial cell; for the treatment or prophylaxis of a pathophysiological condition of the nervous system in a mammal; for the treatment of a tumor; for the treatment of neurofibromatosis; for inhibiting proliferation of a cell; or for stimulating proliferation of a cell.

By "erbB receptor" is meant erbB1 (EGFR), erB2, erbB3, and erbB4 (also HER-1, HER-2, HER-3, and HER-4 of human) existing as monomeric or multimeric (e.g., homodimeric or heterodimeric) cell surface receptor tyrosine kinases that bind to and/or are activated by one or more neuregulins (Meyer et al., *Development* 124: 3575-3586, 1997; Orr-Urtreger et al., *Proc. Natl. Acad. Sci. USA* 90: 1867-71, 1993; Marchionni et al., *Nature* 362: 312-8, 1993; Chen et al., *J. Comp. Neurol.* 349: 389-400, 1994; Corfas et al., *Neuron* 14: 103-115, 1995; Meyer et al., *Proc. Natl. Acad. Sci. USA* 91:1064-1068, 1994; and Pinkas-Kramarski et al., *Oncogene* 15: 2803-2815, 1997). Preferably, the erbB receptors are erbB4 homodimers, erbB2/erbB4 heterodimers, erbB1/erbB3 heterodimers, or any receptor combination that is selective for a NRG-2 polypeptide over a NRG-1 polypeptide or a NRG-3 polypeptide.

By "selective" is meant the preferential binding of an erbB receptor or combination thereof to a NRG-2 polypeptide over a NRG-1 or a NRG-3 polypeptide. More specifically, preferential binding is defined as an increase in the affinity of an erbB receptor to a NRG-2 polypeptide of at least 1.5 fold, more preferably at least 2 fold, relative to the affinity of an erbB receptor to a NRG-1 or NRG-3 polypeptide.

By "neuronal cell" is meant a neuron, nerve cell, neurocyte, or neuronal progenitor cell. A neuronal cell is the morphological and functional unit of the central nervous system and the peripheral nervous system, and includes cholinergic neurons and non-cholinergic neurons.

By "neuronal-associated cell" is meant any non-neuronal cell that is capable of affecting the function of a neuron, or whose function can be affected by a neuron. A neuronal-associated cell includes, but is not limited to, a muscle cell or a nervous system support cell, including a Schwann cell, an astrocyte, an oligodendrocyte, an O-2A progenitor cell, a glial cell (e.g., a radial glial cell or a Bergmann glial cell), a microglial cell, an olfactory bulb ensheathing cell, or a sensory organ cell (e.g., a retinal cell).

By "muscle cell" is meant any cell that contributes to muscle tissue. Muscle tissue is a primary tissue, consisting mainly of specialized contractile cells, and is generally classified as skeletal muscle, cardiac muscle, or smooth muscle. Myoblasts, satellite cells, myotubes, myocytes (e.g., cardiomyocytes), and myofibril tissues are all included in the term "muscle cells," and may all be treated according to the methods of the invention. Muscle cell effects may be induced within skeletal, cardiac, and smooth muscle.

By "neurotrophic agent" or "neurotrophic factor" is meant a substance that elicits a trophic effect in one or more neuronal cells. These effects include, but are not limited to, survival, mitosis, and differentiation. Neurotrophic agents include, but are not limited to, neurotrophins, nerve growth factor, ciliary neurotrophic factor, and brain-derived neurotrophic factor.

By "affecting" is meant the induction of a quantitative change in the response of a target cell, as a result of an interaction with a NRG-2 polypeptide or nucleic acid molecule.

By "cellular communication" is meant the synthesis of a substance (e.g., a neurotrophic agent) in a first cell type (e.g., a neuronal-associated cell) and the interaction of that substance with a second cell type (e.g., a neuronal cell), such that the substance elicits a change in the first or second cell type. Cellular communication includes, but is not limited to, secretion of the substance from a cell. Cellular communication can occur reciprocally or non-reciprocally with one or more cell types.

By "mitogenesis" is meant any cell division that results in the production of new cells in the patient. More specifically, mitogenesis in vitro is defined as an increase in mitotic index, relative to untreated cells, of 50%, more preferably 100%, and most preferably 300%, when the cells are exposed to labeling agent for a time equivalent to two doubling times. The mitotic index is the fraction of cells in culture that have labeled nuclei when grown in the presence of a tracer that only incorporates during S phase (e.g., BrdU), and the doubling time is defined as the average time required for the number of cells in the culture to increase by a factor of two. By "inhibiting mitogenesis" is meant a decrease in the mitotic index, relative to untreated cells, of 50%, more preferably 100%, and most preferably 300%, when the cells are exposed to labeling agent for a time equivalent to two doubling times. Inhibiting mitogenesis also means a cessation of any increase in the mitotic index, relative to control cells.

An effect on mitogenesis in vivo is defined as an increase in cell activation as measured by the appearance of labeled cells in the tissue of a mammal exposed to a tracer that only incorporates during S phase (e.g., BrdU). An useful therapeutic is defined in vivo as a compound that increases cell activation relative to a control mammal by at least 10%, more preferably by at least 50%, and most preferably by more than 200% when the mammal is exposed to labeling agent for a period of greater than 15 minutes and tissues are assayed between 10 hours and 24 hours after administration of the mitogen at the therapeutic dose. For example, in muscle cells, satellite cell activation in vivo may be detected by monitoring BrdU incorporation. Alternatively, satellite cell activation in vivo may be detected by the appearance of the intermediate filament vimentin by immunological or RNA analysis methods. When vimentin is assayed, the useful mitogen is defined as one which causes expression of detectable levels of vimentin in the muscle tissue when the therapeutically useful dosage is provided. Mitogenesis may be induced in, for example, muscle cells of skeletal, cardiac, and smooth muscle, and in glial cells.

By "survival" is meant any process by which a cell avoids death. The term survival as used herein also refers to the prevention of cell loss as evidenced by necrosis, apoptosis, or the prevention of other mechanisms of cell loss. Increasing survival as used herein indicates a decrease in the rate of cell death by at least 10%, more preferably by at least 50%, and most preferably by at least 100% relative to an untreated control. The rate of survival may be measured by counting cells capable of being stained with a dye specific for dead cells (e.g., propidium iodide) in culture. The rate of survival may be measured by counting cells stainable with a dye specific for dead cells (such as propidium iodide) in culture when the cells are 8 days post-differentiation (i.e., 8 days after the medium is changed from 20% to 0.5% serum).

By "growth" is meant the increase in size or number of a cell type relative to a control cell. The therapeutic usefulness of growth increases the size or number of a cell in diseased tissue by at least 10% or more, more preferably by 50% or more, and most preferably by more than 100% relative to the equivalent tissue in a similarly treated control animal. Growth can be measured by, for example, an increase in net weight, protein content, or cell diameter. Muscle growth may occur by the increase in the fiber size and/or by increasing the number of fibers.

By "differentiation" is meant a morphological and/or chemical change that results in the generation of a different cell type or state of specialization. The differentiation of cells as used herein refers to a cellular development program that specifies one or more components of a cell type. The therapeutic usefulness of differentiation increases the quantity of any component of a cell in diseased tissue by at least 10% or more, more preferably by 50% or more, and most preferably by more than 100% relative to the equivalent tissue in a similarly treated control animal.

By "proliferation" is meant the growth or reproduction of similar cells. By "inhibiting proliferation" is meant the decrease in the number of similar cells by at least 10%, more preferably by at least 20%, and most preferably by at least 50%. By "stimulating proliferation" is meant an increase in the number of similar cells by at least 10%, more preferably by at least 20%, and most preferably by at least 50%.

By "inducing myelination" is meant the acquisition, development, or formation of myelin sheath around a nerve fiber. The useful therapeutic for inducing myelination confers an increase in the density of a myelin sheath by at least 10%, more preferably by at least 20%, and most preferably by at least 50%, relative to a control nerve fiber. By "demyelination" is meant the loss of the myelin sheath around a nerve fiber.

By "interacts" is meant contact of a NRG-2 polypeptide with a receptor or other molecule on a target cell.

By "pathophysiological condition" is meant a disturbance of function and/or structure of a living organism, resulting from an external source, a genetic predisposition, a physical or chemical trauma, or a combination of the above, including, but not limited to, any mammalian disease.

By "neuropathy" is meant any disorder affecting the nervous system. A neuropathy may be, for example, a peripheral neuropathy, such a sensory nerve fiber neuropathy or motor fiber neuropathy.

By "cardiomyopathy" is meant a disease that affects the heart muscle. Cardiomyopathy may be primary, i.e., mainly affecting cardiac muscle, or secondary, i.e., affecting cardiac muscle secondary to a systemic disease, infection, or metabolic disease.

By "ischemic damage" is meant damage resulting from decreased blood circulation to cardiac muscle.

By "degenerative congenital disease" is meant a disease that exists at birth, which may be hereditary or due to an influence occurring during gestation, that results in a pathological change in cells or tissues.

By "treatment" is meant the medical management of a patient with the intent to cure, ameliorate, stabilize, or prevent a disease, pathological condition, or disorder. This term includes active treatment, that is, treatment directed specifically toward the improvement or associated with the cure of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. The phrase "treatment" also includes symptomatic treatment, that is, treatment directed toward constitutional symptoms of the associated disease, pathological condition, or disorder.

By "therapeutically-effective amount" is meant an amount of a NRG-2 polypeptide or nucleic acid molecule sufficient to produce a healing, curative, stabilizing, or ameliorative effect in the treatment of a disorder.

By "neurodegenerative disorder" is meant any pathophysiological condition that is characterized by the degeneration of neuronal cells or neuronal-associated cells. The degeneration may include, for example, a decrease in cell number or size, an increase in cell apoptosis or death, or a decrease in cell growth, survival or differentiation.

By "neural regeneration or neural repair" is meant the treatment of a pathophysiological condition by, for example, an increase in neuronal cell or neuronal-associated cell number or size, a decrease in neuronal cell or neuronal-associated cell apoptosis or death, or an increase in neuronal cell or neuronal-associated cell growth, survival or differentiation.

By "inhibits binding" is meant preventing or reducing the binding of a NRG-2 polypeptide to a receptor. The binding is preferably reduced by at least 10%, more preferably by at least 50%, and most preferably by at least 100% relative to a control sample.

By "polypeptide" or "polypeptide fragment" is meant a chain of two or more amino acids, regardless of any post-translational modification (e.g., glycosylation or phosphorylation), constituting all or part of a naturally or non-naturally occurring polypeptide. By "post-translational modification" is meant any change to a polypeptide or polypeptide fragment during or after synthesis. Post-translational modifications can be produced naturally (such as during synthesis within a cell) or generated artificially (such as by recombinant or chemical means). A "protein" can be made up of one or more polypeptides.

The term "identity" is used herein to describe the relationship of the sequence of a particular nucleic acid molecule or polypeptide to the sequence of a reference molecule of the same type. For example, if a polypeptide or nucleic acid molecule has the same amino acid or nucleotide residue at a given position, compared to a reference molecule to which it is aligned, there is said to be "identity" at that position. The level of sequence identity of a nucleic acid molecule or a polypeptide to a reference molecule is typically measured using sequence analysis software with the default parameters specified therein, such as the introduction of gaps to achieve an optimal alignment (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). These software programs match identical or similar sequences by assigning degrees of identity to various substitutions, deletions, or other modifications. Conservative substitutions typically include substitutions within the following groups: glycine, alanine, valine, isoleucine, and leucine; aspartic acid, glutamic acid, asparagine, and glutamine; serine and threonine; lysine and arginine; and phenylalanine and tyrosine.

A nucleic acid molecule or polypeptide is said to be "substantially identical" to a reference molecule if it exhibits, over its entire length, at least 90%, preferably at least 95%, more preferably at least 97%, and most preferably 99% identity to the sequence of the reference molecule. For polypeptides, the length of comparison sequences is at least 16 amino acids, preferably at least 20 amino acids, more preferably at least 25 amino acids, and most preferably at least 35 amino acids. For nucleic acid molecules, the length of comparison sequences is at least 50 nucleotides, preferably at least 60 nucleotides, more preferably at least 75 nucleotides, and most preferably at least 110 nucleotides.

A nucleic acid molecule or polypeptide is "analyzed" or subject to "analysis" if a test procedure is carried out on it that allows the determination of its biological activity or whether it is wild type or mutated. For example, one can analyze the genes of an animal (e.g., a human) by amplifying genomic DNA of the animal using the polymerase chain reaction, and then determining whether the amplified DNA contains a mutation, e.g., by nucleotide sequence or restriction fragment analysis.

By a "substantially pure polypeptide" is meant a polypeptide (or a fragment thereof) that has been separated from proteins and organic molecules that naturally accompany it. Typically, a polypeptide is substantially pure when it is at least 60%, by weight, free from the proteins and naturally-occurring organic molecules with which it is naturally associated. Preferably, the polypeptide is a NRG-2 polypeptide that is at least 75%, more preferably at least 90%, and most preferably at least 99%, by weight, pure. A substantially pure NRG-2 polypeptide can be obtained, for example, by extraction from a natural source (e.g., cerebellum), by expression of a recombinant nucleic acid molecule encoding a NRG-2 polypeptide, or by chemical synthesis. Purity can be measured by any appropriate method, e.g., by column chromatography, polyacrylamide gel electrophoresis, or HPLC analysis.

A polypeptide is substantially free of naturally associated components when it is separated from those proteins and organic molecules that accompany it in its natural state. Thus, a protein that is chemically synthesized or produced in a cellular system different from the cell in which it is naturally produced is substantially free from its naturally associated components. Accordingly, substantially pure polypeptides not only include those derived from eukaryotic organisms, but also those synthesized in E. coli or other prokaryotes.

An antibody is said to "specifically bind" to a polypeptide if it recognizes and binds to the polypeptide (e.g., a NRG-2 polypeptide), but does not substantially recognize and bind to other molecules (e.g., non-NRG-2 related polypeptides) in a sample, e.g., a biological sample, that naturally includes the polypeptide.

By a "transgene" is meant a DNA molecule that is inserted by artifice into a cell (e.g., the nuclear genome of a cell), and is incorporated into the genome of an organism that develops from the cell. Such a transgene can be partly or entirely heterologous (i.e., foreign) to the transgenic organism, or can be a gene that is homologous to an endogenous gene of the organism. An organism or animal (e.g., a mammal, such as a mouse, rat, or goat) can be said to be "transgenic" if it developed from a cell that had a transgene inserted into it by artifice.

By a "knockout mutation" is meant an artificially-induced alteration in a nucleic acid molecule (created by recombinant DNA technology or deliberate exposure to a mutagen) that reduces the biological activity of the polypeptide normally encoded therefrom by at least 80% relative to the unmutated gene. The mutation can be, without limitation, an insertion, deletion, frameshift mutation, or a missense mutation. A "knockout animal" is preferably a mammal, and more preferably a mouse, containing a knockout mutation, as defined above.

By "vector" is meant a genetically engineered plasmid or virus, derived from, for example, a bacteriophage, adenovirus, retrovirus, poxvirus, herpesvirus, or artificial chromosome, that is used to transfer a polypeptide (e.g., a NRG-2 polypeptide) coding sequence, operably linked to a promoter, into a host cell, such that the encoded peptide or polypeptide is expressed within the host cell.

By "promoter" is meant a minimal sequence sufficient to direct or control transcription. Also included are those promoter elements which are sufficient to render promoter-dependent gene expression controllable for cell type or physiological status (e.g., hypoxic versus normoxic conditions), or inducible by external signals or agents; such elements may be located in the 5' or 3' or internal regions of the native gene.

By "operably linked" is meant that a nucleic acid encoding a polypeptide (e.g., a cDNA) and one or more regulatory sequences are connected in such a way as to permit gene expression when the appropriate molecules (e.g., transcriptional activator proteins) are bound to the regulatory sequences.

By "NRG-2 polypeptide producing cell" is meant a cell (or a descendent of a cell) into which a DNA molecule encoding a NRG-2 polypeptide has been introduced, by means of recombinant DNA techniques or known gene therapy techniques.

The invention provides several advantages. For example, it provides methods and reagents that can be used in the diagnosis and treatment of diseases that are sensitive to the bioactivities of NRG-2 polypeptides. Other features and advantages of the invention will be apparent from the detailed description of the invention, the drawings, and the claims.

BRIEF DESCRIPTION OF THE DRAWINGS

FIG. 3A shows a western blot analysis of conditioned media (cm) and cell lysates (cells) from mock-(vector) or rhNRG-2α-transfected CHO/S cells.

FIG. 3B shows a western blot analysis of conditioned media from mock-(vec), rhNRG-2α (α), or rhNRG-2β-transfected (β) CHO/S cells.

FIG. 3C shows a western blot analysis of conditioned media from CHO cells expressing rat NRG-2β.

FIG. 11A shows a photograph indicating BrdU incorporation in neural cells, including neural progenitor cells, cultured with rhNRG-2β.

FIG. 11B shows a bar graph indicating the effect of rhNRG-2β on BrdU incorporation.

DETAILED DESCRIPTION OF THE INVENTION

Figure 1:
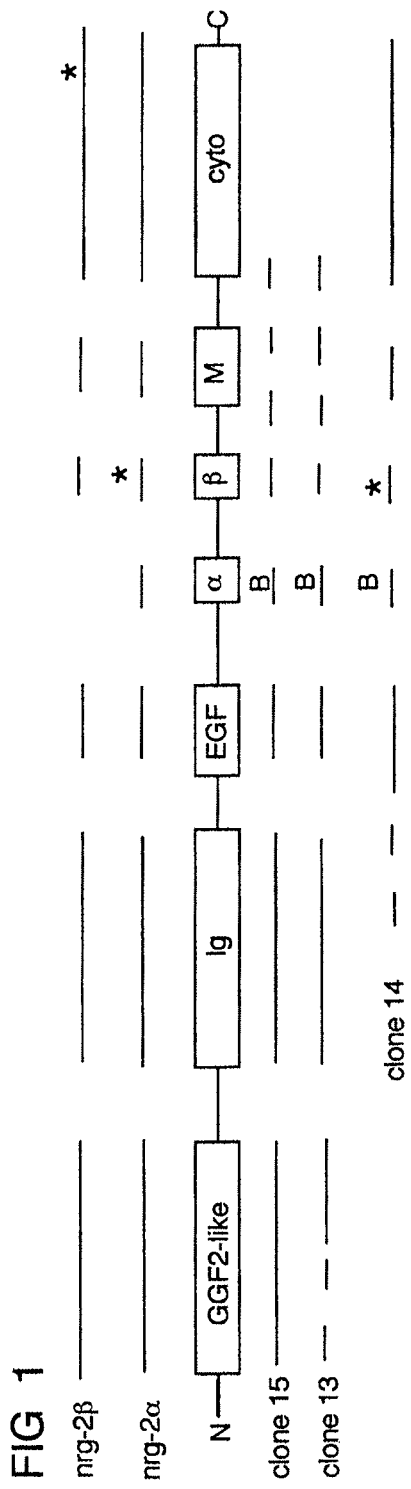
FIG. 1 shows a schematic diagram of NRG-2 gene products and human cDNA clones.

The invention provides NRG-2 polypeptides and nucleic acid molecules, antibodies that bind these NRG-2 polypeptides, and therapeutic and diagnostic methods employing NRG-2 polypeptides and nucleic acid molecules.
Bioassays NRG-2 ligands and erbB receptors are expressed in the nervous system, in neural precursors and neurons of brain, spinal cord and retina; skeletal and cardiac muscle; lung; thymus, kidney; adrenal glands; skin; breast epithelia; and other organs during embryonic development and in adult tissues. Major sites of NRG-2 expression include the cerebellum (Purkinje and granule cells), olfactory bulb, dentate gyrus, pyramidal cells of the occipital cortex, lung, and thymus. The expression patterns of NRG-2 receptors in specific cells and tissues are used to identify cellular targets of NRG-2 actions, and to identify bioactivities that are relevant to specific NRG-2-related diseases, such as demyelinating disorders of the peripheral and central nervous systems; neuropathies; neurodegenerative disorders; cardiomyopathies; loss of hearing, balance or vision; pain; neurotrauma; cancer; sensorineural hearing loss or sensorineural balance loss from viral infection, aging, or antibiotics (e.g. aminoglycosides); retinopathy (e.g., hypertensive, diabetic, occlusive, macular degeneration, retinitis pigmentosa, optic neuropathy, injury); Guillaime Barre disease; stroke; or brain or spinal cord injury. Many of the NRG-2-responsive cell types in embryonic, neonatal, and adult tissues express the receptor combinations of erbB2/erbB3, erbB2/erbB4, or erbB4 alone. For example, peripheral nervous system (PNS) and central nervous system (CNS) glial cell types express erbB2; Schwann cells also express erbB3. In the CNS, erbB4 and erbB3 have been observed on various glial cell types, including astrocytes, oligodendrocyte progenitors, radial glia in the developing cortex, and Bergmann glia in the cerebellum. The erbB2/erbB4 combination is found in ventricular cardiomyocytes.

Therapeutic and diagnostic utilities for NRG-2 polypeptides are identified by, for example, conducting bioassays in vitro. Culture systems that reflect NRG-2 expression patterns, along with the distribution of particular receptors, such as erbB2/erbB4 or erbB4 alone, which are examples of erbB receptor combinations that may show a preference for NRG-2 over NRG-1, are selected. For example, NRG-2 bioactivities are evaluated using CNS glia, such as oligodendrocytes and olfactory bulb ensheathing cells, mid-brain dopaminergic neurons, cerebellar granule neurons, and cardiomyocytes. These cell populations express NRG receptors, and respond to treatment with one or more isoforms of NRG-1 in a variety of quantitative bioassays. The activities of NRG-2 (e.g. rhNRG-2α, rhNRG-2β) and NRG-1 (e.g., rhGGF2) isoforms are compared, using sister cultures, in various dose-response assays, including but not limited to, stimulation of proliferation, survival, differentiation, migration, and morphological changes. The relative potencies of the NRG-2 and NRG-1 isoforms are determined on the basis of, for example, protein concentration.

Diagnostic Methods Employing NRG-2 Nucleic Acid Molecules, Polypeptides, and Antibodies NRG-2 nucleic acid molecules, polypeptides, and antibodies are used in methods to diagnose or monitor a variety of diseases and conditions, including those involving mutations in, or inappropriate expression of, NRG-2 genes. NRG-2 expression has been documented in a variety of tissues, as discussed above. Thus, detection of abnormalities in NRG-2 genes or their expression are used in methods to diagnose, or to monitor treatment or development of diseases of these tissues.

The diagnostic methods of the invention are used, for example, with patients that have a cardiovascular or a neurological disease, in an effort to determine its etiology, and thus, to facilitate selection of an appropriate course of treatment. The diagnostic methods are also used with patients that have not yet developed a cardiovascular or neurological disease, but who may be at risk of developing such a disease, or with patients that are at an early stage of developing such a disease. Many cardiovascular and neurological diseases occur during development, and thus, the diagnostic methods of the invention are also carried out on a fetus or embryo during development. Also, the diagnostic methods of the invention are used in prenatal genetic screening, for example, to identify parents who may be carriers of a recessive NRG-2 mutation.

NRG-2 abnormalities that are detected using the diagnostic methods of the invention include those characterized by, for example, (i) abnormal NRG-2 polypeptides, (ii) NRG-2 genes containing mutations that result in the production of such polypeptides, and (iii) NRG-2 mutations that result in production of abnormal amounts of NRG-2.

Levels of NRG-2 expression in a patient sample are determined by using any of a number of standard techniques that are well known in the art. For example, NRG-2 expression in a biological sample (e.g., a blood or tissue sample, or amniotic fluid) from a patient is monitored by standard northern blot analysis or by quantitative PCR (see, e.g., Ausubel et al., *Current Protocols in Molecular Biology*, John Wiley & Sons, New York, N.Y., 1998; *PCR Technology: Principles and Applications for DNA Amplification*, H. A. Ehrlich, Ed., Stockton Press, NY; Yap et al. *Nucl. Acids. Res.* 19:4294, 1991).

Therapeutic Methods Employing NRG-2 Nucleic Acid Molecules, Polypeptides, and Antibodies The invention includes methods of treating or preventing NRG-2-related diseases. Therapies are designed to circumvent or overcome a NRG-2 gene defect, or inadequate or excessive NRG-2 gene expression, and thus modulate and possibly alleviate conditions involving defects in NRG-2 genes or proteins. In considering various therapies, it is understood that such therapies are, preferably, targeted to the affected or potentially affected organs, for example, the heart or the nervous system. Reagents that are used to modulate NRG-2 biological activity can include, without limitation, full length NRG-2 polypeptides; NRG-2 cDNA, mRNA, or antisense RNA; NRG-2 antibodies; and any compound that modulates NRG-2 biological activity, expression, or stability.

Treatment or prevention of diseases resulting from a mutated NRG-2 gene is accomplished, for example, by replacing a mutant NRG-2 gene with a normal NRG-2 gene, administering a normal NRG-2 gene, modulating the function of a mutant NRG-2 protein, delivering normal NRG-2 protein to the appropriate cells, or altering the levels of normal or mutant NRG-2 protein. It is also possible to correct a NRG-2 defect to modify the physiological pathway (e.g. a signal transduction pathway) in which the NRG-2 protein participates.

Gene transfer is achieved using viral vectors, as well as non-viral means involving transfection in vitro by means of any standard technique, including but not limited to, calcium phosphate, DEAE dextran, electroporation, protoplast fusion, and liposomes. Transplantation of normal genes into the affected tissues of a patient can also be accomplished by transferring a normal NRG-2 gene into a cultivatable cell type ex vivo, after which the cell (or its descendants) is injected into a targeted tissue. Another strategy for inhibiting NRG-2 function using gene therapy involves intracellular expression of an anti-NRG-2 antibody or a portion of an NRG-2 antibody. For example, the gene (or gene fragment) encoding a monoclonal antibody that specifically binds to NRG-2 and inhibits its biological activity is placed under the transcriptional control of a tissue-specific gene regulatory sequence. Another therapeutic approach involves administration of recombinant NRG-2 polypeptide, either directly to the site of a potential or actual disease-affected tissue (for example, by injection) or systemically (for example, by any conventional recombinant protein administration technique). The dosage of systemically delivered NRG-2 depends on a number of factors, including the size and health of the individual patient but, generally, between about 0.006 mg/kg to about 0.6 mg/kg, inclusive, is administered per day to an adult in any pharmaceutically acceptable formulation. Dosages of NRG-2 delivered by local delivery may differ from systemic delivery, and can be determined using standard techniques known to those of ordinary skill in the art.

In a patient diagnosed as having a NRG-2 mutation or NRG-2-related disease, or as susceptible to NRG-2 mutations, aberrant NRG-2 expression (even if those mutations or expression patterns do not yet result in alterations in NRG-2 expression or biological activity), or to a NRG-2-related disease, any of the above-described therapies are administered before the occurrence of the disease phenotype. Also, compounds shown to modulate NRG-2 expression or NRG-2 biological activity are administered to patients diagnosed with potential or actual diseases by any standard dosage and route of administration. Alternatively, gene therapy using an antisense NRG-2 mRNA expression construct is undertaken to reverse or prevent the gene defect prior to the development of the full course of the disease.

The therapeutic methods of the invention are, in some cases, targeted to prenatal treatment. For example, a fetus found to have a NRG-2 mutation is administered a gene therapy vector including a normal NRG-2 gene or normal NRG-2 protein. Such treatment may be required only for a short period of time, or may, in some form, be required throughout such a patient's lifetime. Any continued need for treatment, however, is determined using, for example, the diagnostic methods described above. Also as discussed above, NRG-2 abnormalities may be associated with diseases in adults, and thus, adults are subject to the therapeutic methods of the invention as well.

Identification of Molecules that Modulate NRG-2 Biological Activity or Whose Biological Activity is Modulated by NRG-2

Isolation of NRG-2 cDNAs (as described herein) also facilitates the identification of molecules that increase or decrease NRG-2 biological activity. Similarly, molecules whose activity is modulated by NRG-2 biological activity can be identified. According to one approach, candidate molecules are added at varying concentrations to the culture medium of cells expressing NRG-2 mRNA. NRG-2 biological activity is then measured using standard techniques. The measurement of biological activity can include, without limitation, the measurement of NRG-2 protein and nucleic acid molecule levels, and NRG-2 phosphorylation.

If desired, the effect of candidate modulators on expression can also be measured at the level of NRG-2 protein production using the same general approach and standard immunological detection techniques, such as western blotting or immunoprecipitation with a NRG-2-specific antibody (see below).

A test compound that is screened in the methods described above can be a chemical, be it naturally-occurring or artificially-derived. Such compounds can include, for example, polypeptides, synthesized organic molecules, naturally occurring organic molecules, nucleic acid molecules, and components thereof. Candidate NRG-2 modulators include peptide as well as non-peptide molecules (e.g., peptide or non-peptide molecules found, e.g., in a cell extract, mammalian serum, or growth medium in which mammalian cells have been cultured).

Administration of NRG-2 Polypeptides, NRG-2 Nucleic Acid Molecules, and Modulators of NRG-2 Synthesis or Function A NRG-2 protein, nucleic acid molecule, modulator, neutralizing NRG-2 antibody, or NRG-2-inhibiting compound (e.g., antisense NRG-2 or a NRG-2 dominant negative mutant) is administered within a pharmaceutically-acceptable diluent, carrier, or excipient, in unit dosage form to patients or experimental animals. Also, conventional pharmaceutical practice is employed to provide suitable formulations or compositions in which to administer such molecules or compounds to patients suffering from a NRG-2-related disease, such as demyelinating disorders of the peripheral and central nervous systems; neuropathies; neurodegenerative disorders; cardiomyopathies; loss of hearing, balance or vision; pain; neurotrauma; cancer; sensorineural hearing loss or sensorineural balance loss from viral infection, aging, or antibiotics (e.g. aminoglycosides); retinopathy (e.g., hypertensive, diabetic, occlusive, macular degeneration, retinitis pigmentosa, optic neuropathy, injury); Guillaime Barre disease; stroke; or brain or spinal cord injury. Administration can begin before or after the patient is symptomatic.

Any appropriate route of administration can be employed, for example, administration can be parenteral, intravenous, intra-arterial, subcutaneous, intramuscular, intracranial, intraorbital, ophthalmic, intraventricular, intracapsular, intraspinal, intracisternal, intraperitoneal, intranasal, inhalation to deep lung, aerosol, by suppositories, oral, or topical (e.g. by applying an adhesive patch carrying a formulation capable of crossing the dermis and entering the bloodstream). Preferably, the administration is local to the afflicted tissue, such as cardiac, lung, or nerve tissue. Therapeutic formulations can be in the form of liquid solutions or suspensions; for oral administration, formulations can be in the form of tablets or capsules; and for intranasal formulations, in the form of powders, nasal drops, or aerosols. Any of the above formulations may be a sustained-release formulation.

Methods that are well known in the art for making formulations are found, for example, in *Remington's Pharmaceutical Sciences*, (18$^{th}$ edition), ed. A. Gennaro, 1990, Mack Publishing Company, Easton, Pa. Formulations for parenteral administration can, for example, contain excipients; sterile water; or saline; polyalkylene glycols, such as polyethylene glycol; oils of vegetable origin; or hydrogenated napthalenes. Sustained-release, biocompatible, biodegradable lactide polymer, lactide/glycolide copolymer, or polyoxyethylene-polyoxypropylene copolymers can be used to control the release of the compounds. Other potentially useful parenteral delivery systems for NRG-2 modulatory compounds include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate, and deoxycholate, or can be oily solutions for administration in the form of nasal drops, or as a gel.

Synthesis of NRG-2 Proteins, Polypeptides, and Polypeptide Fragments

Those skilled in the art of molecular biology will understand that a wide variety of expression systems can be used to produce the recombinant NRG-2 proteins. The precise host cell used is not critical to the invention. The NRG-2 proteins can be produced in a prokaryotic host (e.g., *E. coli*) or in a eukaryotic host (e.g., *S. cerevisiae*, insect cells such as Sf9 cells, or mammalian cells such as COS, NIH 3T3, CHO, or HeLa cells). These cells are commercially available from, for example, the American Type Culture Collection, Rockville, Md. (see also Ausubel et al., *Current Protocols in Molecular Biology*, John Wiley & Sons, New York, N.Y., 1998). The method of transformation and the choice of expression vehicle (e.g., expression vector) will depend on the host system selected. Transformation and transfection methods are described, e.g., in Ausubel et al., *Current Protocols in Molecular Biology*, John Wiley & Sons, New York, N.Y., 1998, and expression vehicles can be chosen from those provided, e.g. in Pouwels et al., *Cloning Vectors: A Laboratory Manual*, 1985, Supp. 1987).

The characteristics of NRG-2 nucleic acid molecules are analyzed by introducing such genes into various cell types or using in vitro extracellular systems. The function of NRG-2 proteins produced in such cells or systems are then examined under different physiological conditions. Also, cell lines can be produced that over-express the NRG-2 gene product, allowing purification of NRG-2 for biochemical characterization, large-scale production, antibody production, and patient therapy.

Use of NRG-2 Antibodies

Antibodies to NRG-2 proteins (for example, those described herein) are used to detect NRG-2 proteins or to inhibit the biological activities of NRG-2 proteins. For example, a nucleic acid molecule encoding an antibody or portion of an antibody can be expressed within a cell to inhibit NRG-2 function. In addition, the antibodies can be coupled to compounds, such as radionuclides and liposomes for diagnostic or therapeutic uses. Antibodies that inhibit the activity of a NRG-2 polypeptide can also be useful in preventing or slowing the development of a disease caused by inappropriate expression of a wild type or mutant NRG-2 gene.

Construction of Transgenic Animals and Knockout Animals

Characterization of NRG-2 genes provides information that allows NRG-2 knockout animal models to be developed by homologous recombination. Preferably, a NRG-2 knockout animal is a mammal, most preferably a mouse. Similarly, animal models of NRG-2 overproduction can be generated by integrating one or more NRG-2 sequences into the genome of an animal, according to standard transgenic techniques. Moreover, the effect of NRG-2 gene mutations (e.g., dominant gene mutations) can be studied using transgenic mice carrying mutated NRG-2 transgenes or by introducing such mutations into the endogenous NRG-2 gene, using standard homologous recombination techniques.

A replacement-type targeting vector, which can be used to create a knockout model, can be constructed using an isogenic genomic clone, for example, from a mouse strain such as 129/Sv (Stratagene Inc., LaJolla, Calif.). The targeting vector can be introduced into a suitably-derived line of embryonic stem (ES) cells by electroporation to generate ES cell lines that carry a profoundly truncated form of a NRG-2 gene. To generate chimeric founder mice, the targeted cell lines are injected into a mouse blastula-stage embryo. Heterozygous offspring can be interbred to homozygosity. NRG-2 knockout mice provide a tool for studying the role of NRG-2 in embryonic development and in disease. Moreover, such mice provide the means, in vivo, for testing therapeutic compounds for amelioration of diseases or conditions involving a NRG-2-dependent or NRG-2-affected pathway.

The following Examples will assist those skilled in the art to better understand the invention and its principles and advantages. It is intended that these Examples be illustrative of the invention and not limit the scope thereof.

Example 1

Cloning of Human NRG-2 cDNA

A full-length cDNA encoding NRG-2a was identified from cerebellum. Multiple probes to various regions of NRG-2 coding sequences were designed based on rodent and human sequence data for cloning, mapping and sequence analysis. Prior to screening libraries, the specificity of the probes was confirmed by analyzing human cerebellar RNA using a 3' RACE (rapid amplification of cDNA ends) approach. Approximately 400,000 cDNAs from two human cerebellum γt10 cDNA libraries (Clontech Laboratories, Palo Alto, Calif.; Catalog No. HL1128a) were screened with an oligonucleotide probe: 5' GCA TCA ACC AGC TCT CCT GC 3' (SEQ ID NO: 5) from the EGFL domain of NRG-2. Twenty five hybridization signals were detected; twenty of the phage clones corresponding to these signals were cloned and further analyzed by hybridization studies, physical mapping, and DNA sequencing. The results of these analyses were consistent with the existence of multiple structural variants (isoforms) among the human NRG-2 clones that were identified. Preliminary structural information on the clones was obtained by filter hybridization to phage plaques and restriction endonuclease analyses of the cDNA inserts. PCR studies, using internal primers, in pairs or in combination with flanking sequences, were used to obtain physical mapping data (see Table 1).

The primers used were as follows:

```
                                           (SEQ ID NO: 6)
Primer 1471: 5'-GCA TCA ACC AGC TCT CCT GC-3'

(SEQ ID NO: 7)
Primer 1494: 5'-TGC GAA CTG CTG ACA CCT GT-3'

(SEQ ID NO: 8)
Primer 1527: 5'-CCA CCT TTT GAG CAA GTT CAG-3'

(SEQ ID NO: 9)
Primer 1528: 5'-GAG GTG GCT TAT GAG TTC TTC-3'

(SEQ ID NO: 10)
Primer 1531: 5'-GGC CAC CAC ACA GAC GAT G-3'
```

First, the insert sizes, which ranged from 0.8 kb to 3.3 kb (average size was roughly 1.7 kb), were analyzed. NRG-2 transcripts contain an EGFL domain and cytoplasmic sequences that exhibit much of the structural diversity of these polypeptides, and this specific internal region was focused on next to map the clones by PCR analysis. This analysis yielded four groups of products, and multiple clones were identified in each group. Therefore, the four groups (A-D) are likely to represent the extent of structural diversity in this region among the NRG-2 gene products in human cerebellum. Four clones (group A) gave no product in this experiment. This result was consistent with the data from hybridization experiments, which had shown that these clones lacked the sequence of the downstream primer (in the cytoplasmic domain). In the third experiment, the orientation of the clones was determined and the distance from the EGFL domain to the ends of the clones was estimated by using primers in the EGFL domain in combination with primers from flanking sequences in the phage arms. These studies, therefore, enabled the segregation of the NRG-2 cDNAs into groups, and facilitated identification of potential full-length cDNAs encoding secretable isoforms of human NRG-2.

TABLE 1

Mapping human NRG-2 cerebellar cDNA clones

| Group: clones | Internal Product[1] | Largest Clone: size[2] | 5' end to EGFL[3] | EGFL to 3' end[4] |
|---|---|---|---|---|
| A: 1, 4, 13, 15 | None | 13: 3300 | 1400 | 2300 |
| B: 3, 6, 7, 9, 11, 18, 20 | 170 | 11: 1050 | 600 | 450 |
| C: 10, 12, 14, 16 | 260 | 14: 1500 | 850 | 650 |
| D: 5, 8, 17, 19 | 650 | 8: 1600 | 800 | 800 |

PCR analyses of cDNA clones: products were sized on 6% polyacrylamide gels; the table showns sizes in base pairs.
[1]Upstream primer 1471 from EGFL domain; downstream primer 1531 from cytoplasmic domain.
[2]Primers 1527, 1528 from flanking sequences in λgt10.
[3]Upstream primer 1527 from flanking sequences in λgt10; downstream primer 1494 from EGFL domain.
[4]Upstream primer 1471 from EGFL domain; downstream primer 1528 from flanking sequences in λgt10.

Example 2

Human NRG-2 DNA Sequence Analysis

To obtain a more complete picture of the different structures, DNA sequencing was undertaken on representative clones from each group using a cycle sequencing protocol and the same primers used for the PCR analysis described above. Comparison of the sequence contigs surrounding the EGFL domain (from groups B-D) to each other and to rat and human NRG-2 sequences led to several conclusions.

First, the group B clones matched the NRG-2β cDNA structure. These sequences connected the EGFL domain to the transmembrane and cytoplasmic domains, and thus encoded membrane-attached NRG-2 protein. Second, all of the group C structures contained both the α and the β sequences, and matched the structure of the NRG-2α cDNA. Therefore, group C clones should encode a secreted NRG-2 protein. Clone 14 appeared to be the best candidate for a full-length version of this structure. In group D, both α and β sequences were present, but they were not adjacent. A 450 bp sequence intervening between these two known coding sequences was found, and immediately adjacent to the regions identified as α and β sequences were canonical splice junction donor (GT) and acceptor (AG) sequences. Thus, this structure probably represents a partially spliced transcript of the NRG-2 gene.

Given this information, it appeared that secretable forms of NRG-2 were most likely be found in the clones of groups A and C. Clone 14 served as a suitable representative of group C. Two group A clones were advanced in parallel; clone 13 was selected because of the relatively large insert size and clone 15 was pursued because of the presence of sequence 5' of the EGFL domain that was detected in hybridization experiments. When sequences of clones 13, 14 and 15 were completed it became apparent that none of them alone encoded a full length human NRG-2a. However, given the substantial overlap in the structure of these clones, it was clear that portions of each could be spliced together to generate one full length clone encoding NRG-2a. FIG. 1 shows a schematic representation of the structure of these sequences; coding segments of the NRG-2 gene are shown in the shaded boxes, and the coding sequences (solid lines) that are present in described NRG-2α and NRG-2β isoforms are drawn above; isoforms of NRG-2 contain GGF2-like, immunoglobulin-like (Ig), EGF-like (EGFL), α, β, transmembrane (M), and cytoplasmic (cyto) domains; stop codons are indicated by (*); and putative intron sequences are represented by dashed lines. A unique BsrGI site (B) present in the α coding segment was used to construct a full-length human NRG-2α cDNA by connecting 5' sequences of clone 15 to the 3' sequences of clone 14, and the sequence of the final construct was determined.

The major open reading frame of the NRG-2a cDNA (SEQ ID NO: 1) encodes a 330 amino acid protein (SEQ ID NO: 2).

Example 3

Cloning and Construction of Human NRG-2β cDNA

The human NRG-2β cDNA is constructed partly from the human NRG-2a cDNA (the vector and the 5' 869 bp of sequence encoding the N-terminus of human NRG-2, which is present in both the α and the β isoforms) and partly from a phage clone (e.g., phage clone 11 was shown in mapping studies to contain the β sequence—see Table 1, Example 1, and Example 2) containing a partial human cDNA encoding human NRG-2β (two 3' fragments: one contains the β sequence and the other a stop codon).

The human NRG-2α cDNA (Example 2) can be digested with enzymes Not I and Xba I (New England Biolabs, Beverly, Mass.) to generate a 5500 bp vector and a 1555 bp insert containing the cDNA. Both fragments are recovered from a gel of 1% agarose in TAE buffer using the QIAEX II Agarose Gel Extraction kit and protocol (Qiagen, Inc., Valencia, Calif.). The insert fragment (1555 bp) is further digested using Drd I (New England Biolabs, Beverly, Mass.) to generate a 5' 869 bp fragment and a 3' fragment of approximately 700 bp. The 869 bp Not I-Drd I fragment is recovered from a gel of 2% agarose in TAE buffer using the QIAEX II Agarose Gel Extraction kit and protocol (Qiagen, Inc., Valencia, Calif.). This 869 bp fragment contains the initiator methionine and encodes the N-terminal portion of human NRG-2β. It is ligated into the 5550 bp vector along with two additional fragments, which are derived from cDNAs that have sequences of human NRG-2β as described below.

The major difference between the human NRG-2α and human NRG-2β sequences reside between the single Drd I and Bsr DI sites. The α isoform contains a 77 bp coding segment that is spliced into the β isoform sequence. To obtain the sequences encoding human NRG-2β, a 113 bp Drd I-BsrDI fragment, which is 77 bp shorter than the corresponding sequence of human NRG-2α, is generated from phage clone 11 as follows. Primers (1551: 5'-GTG-AGC-ACC-ACC-CTG-TCA-TC-3', SEQ ID NO: 11; 1546: 5'-GAG-CTA-GTC-TAG-AGT-GGC-TTA-TGA-GTA-TTT-CTT-C-3', SEQ ID NO: 12) flanking the Drd I and BsrDI sites are used to amplify the phage clone 11 DNA template following methods recommended by the supplier of Taq Polymerase (Perkin Elmer/Roche, Branchburg, N.J.). The PCR product is precipitated with ethanol, then digested sequentially using Drd I and BsrDI to produce a 113 bp fragment. Similarly, the 3' fragment also is derived by PCR implication of the phage clone 11 template using primers 1550 and 1546. Primer 1550 (5'-CAG-CAG-TTC-GCA-ATG-GTC-AAC-TTC-TCC-TAA-GCA-CC-3', SEQ ID NO: 13) is positioned to cross over the BsrDl site and contains an insertion of a single T that will mutate the target sequence 5'-CAG-CAG-TTC-GCA-ATG-GTC-AAC-TTC-TCC-AAG-CAC-C-3', SEQ ID NO: 14, to 5'-CAG-CAG-TTC-GCA-ATG-GTC-AAC-TTC-TCC-TAA-GCA-CC-3', SEQ ID NO: 15, and thus, convert a lysine codon to a TAA stop codon. Primer 1546 is targeted to the phage right arm cloning site and contains an Xba I site. Digestion of the product using BsrDI and Xba I generates a 425 bp fragment that becomes the 3' end of the human NRG-2β cDNA. Both the 113 bp and 425 bp fragments are recovered from 2% agarose gels.

The recovery of fragments is quantified by electrophoresis relative to double stranded DNA markers of known length and quantity (e.g., phage lambda Hind III digest; New England Biolabs, Beverly, Mass.; pGEM markers, Promega, Madison, Wis.), and then each purified fragment is converted into molar equivalents. The purified vector (100 ng) and the three fragments are ligated together (T4 DNA ligase; New England Biolabs, Beverly, Mass.) at equimolar ratios according to instructions provided by the supplier. The ligations are used to transform competent bacterial cells, such as *E. coli* XL1 Blue (Stratagene, La Jolla, Calif.) according to instructions provided by the supplier. Colonies containing the vector are selected on the basis of resistance to 50 ug/ml ampicillin, and the structure of the human NRG-2β cDNA is analyzed by PCR amplification and DNA sequencing of plasmid DNA. The major open reading frame of the human NRG-2β cDNA (SEQ ID NO: 3) encodes a protein of 298 amino acids (SEQ ID NO: 4).

Example 4

Expression of Human NRG-2

Figure 2:
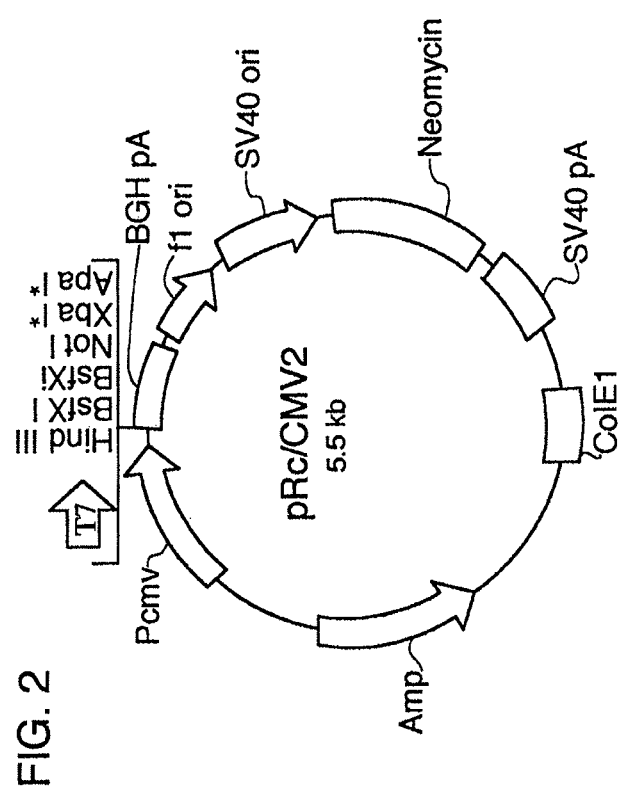
FIG. 2 shows a schematic diagram of the mammalian expression vector pRc/CMV2.

A vector for transient and stable expression of human NRG-2 in mammalian cells was constructed. The pRc/CMV2 vector (Invitrogen V750-20; see FIG. 2) was used to express human NRG-2. This 5.5 kb vector utilizes a CMV promoter and a bovine growth hormone polyadenylation site to drive high level constitutive expression in both transient and stable transfections. Neomycin selection (G418) can be used to select for stable transformants. The human NRG2-α cDNA sequence (SEQ ID NO: 1) was cloned directionally into the polylinker using the Hind III and Xba I sites. The cDNA insert of the final construct was sequenced on both strands. The human NRG-2 expression vectors were then expressed in CHO cells to provide a reliable source of recombinant human protein.

Both human NRG-2 α and β cDNAs were transiently transfected into CHO/S cells (Life Technologies, Inc., Rockville, Md.). Heterologous expression of transfected genes was performed to ensure the proper functioning of the CHO/S cell system. Mock transfections were performed in parallel. Transfections were done in 100 mm dishes (in triplicate) by the Lipofectamine™ 2000 method according to protocols supplied by the manufacturer (Life Technologies, Inc., Rockville, Md.). Cell lysates and conditioned media samples were collected 3 or 4 days post-transfection. To prepare lysates, cell monolayers were washed with PBS, scraped from the dishes, and lysed by three freeze-thaw cycles in 150 μl 0.25 M Tris HCl pH 8. Cell debris was pelleted and the supernatant recovered. Conditioned media samples were collected, then either analyzed directly or concentrated and buffer-exchanged with 10 mM Tris HCl, pH 7.4 using Centricon-10 units (Ambion). Secretion of biologically active recombinant human NRG-2 gene product was demonstrated by stimulation of Schwann cell proliferation following transient transfection of CHO/S cells and detection of NRG-2 bioactivity in the conditioned media as compared to the cell lysate (Marchionni et al., *Nature* 362: 312-8, 1993).

The recombinant human NRG-2 (rhNRG-2) proteins were efficiently expressed in the conditioned media of the transfected cells (FIGS. 3A and 3B), indicating these proteins can be successfully secreted from mammalian cells. In FIG. 3A, the conditioned media, but not the cell lysate from cells transfected with rhNRG-2α (and not from mock-transfected cells) expressed a specific immunoreactive band running at ca. 56 kD. In FIG. 3B, both the α and β isoforms were secreted into the conditioned media of transfected CHO/S cells (note the smaller rhNRG-2β protein (298 amino acids) ran faster (ca. 47 kD) than the rhNRG-2α protein (331 amino acids), as expected).

After confirming the bioactivity of the expression construct in transient transfections, stable CHO/S cell lines were generated to express rhNRG-2β. The pRc/CMV2 vector contains a Neomycin resistance gene, so stably-transformed cells can be selected in media that contain an effective concentration of G418. Following transfection of recipient CHO/S cells, well-isolated colonies that survived 11 days in the selective media were picked using cloning rings. Cell lines showing the highest level expression of rhNRG-2β and G418 resistance were continued for further evaluation. Three useful properties of cell lines are sustained viability, adaptation to serum-free (or low serum) media, and expression level of recombinant protein. Thus, several of the lines were expanded in parallel and tested for adaptation to serum-free growth conditions and expression of rhNRG-2β by western blot. Western blot analysis showed that Dulbecco's modified essential medium supplement with 2% fetal calf serum provided for optimum expression of rhNRG-2β in these experiments. Bioactivity was assayed on expressed material from the leading candidate lines. Two isolates were cloned by limiting dilution, and a single isolated cell line was used for further studies.

Figure 6:
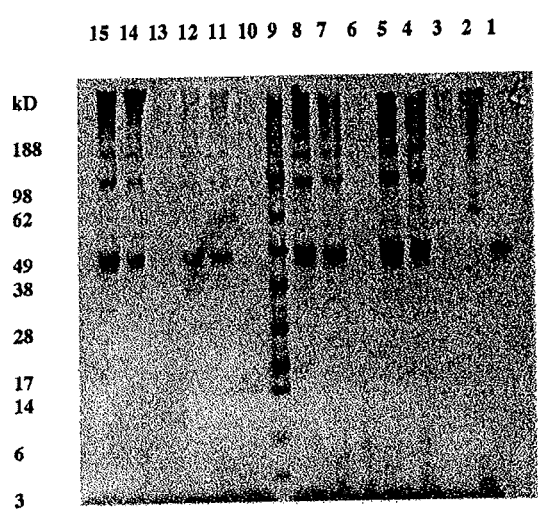
FIG. 6 shows a western blot analysis of stable transfectants used for methotrexate selection.

In addition to generating stable CHO/S cell lines expressing NRG-2 proteins, a strategy relying on the co-amplification of integrated copies of rhNRG-2β expression constructs and a transfected dihydrofolate reductase (dhfr) gene was developed. Mammalian expression vectors were constructed in pcDNA3.1 (Invitrogen) and pMACSK$^k$.II (Miltenyi Biotec Ltd.) under the control of the CMV and SV40 promoters, respectively. These vectors were co-transfected along a dhfr expression vector into CHO-dhfr cells and thirty colonies resistant to G418 were selected, grown up and expression levels were analyzed by western blot (FIG. 6) and RT/PCR. FIG. 6 Lane 1 shows rhNRG-2β control sample, Lane 2 shows CHO SD (US) rhNRG2β 48 hr supernatant, Lanes 3-5 show 24-72 hrs Clone T3B2, Lanes 6-8 show 24-72 hrs Clone T3B1, Lane 9 shows molecular weight markers (Invitrogen cat # LC5925), Lanes 10-12 show 24-72 hrs Clone T3A6, and Lanes 13-15 show 24-72 hrs Clone T3A5. The T3B2, T3B1, T3A5 clones were selected for dilution cloning and for amplification/selection. Gene co-amplification is induced by step-wise increase in methotrexate concentrations and clones are monitored for increases in yield of secreted rhNRG2β.

Example 5

Generation and Testing of Antisera to Detect Expressed NRG-2 Protein

A polyclonal antiserum that specifically detects expressed NRG-2 protein was generated as follows. Peptides were designed from the deduced human and rat NRG-2 sequences to generate rabbit polyclonal antisera to be used to monitor NRG-2 levels in expression and purification samples.

The peptides used were as follows:

```
                                       (SEQ ID NO: 16)
    K71983M:        APLERNQRYIFFLEPTEQPLVFK (SEQ ID NO: 17)
    K71984M:        NSRLQFNKVKVEDAGEY (SEQ ID NO: 18)
    K71985K:        NGGVCYYIEGINQLS
```

One of these peptides (K71984M), derived from the Ig domain sequence, which is identical in the deduced rat and human NRG-2 sequences, produced useful sera for western blotting recombinant rat NRG-2β in conditioned media from transfected CHO cells (see FIG. 3C) and did not cross-react with rhGGF2. These NRG-2 antisera were purified against the immobilized peptide. FIG. 3C shows a western blot analysis of conditioned media from CHO cells expressing rat NRG-2β. The lanes contain either 20 μl of 15-fold concentrated conditioned medium from CHO cells expressing rrNRG-2β (left) or 10 ng rhGGF2 (right). Anti-NRG-2 serum was used at 1 μg/ml and specifically detected rrNRG-2β, at 46 kD, but not rhGGF2, which runs at 80 kD.

Figure 5:
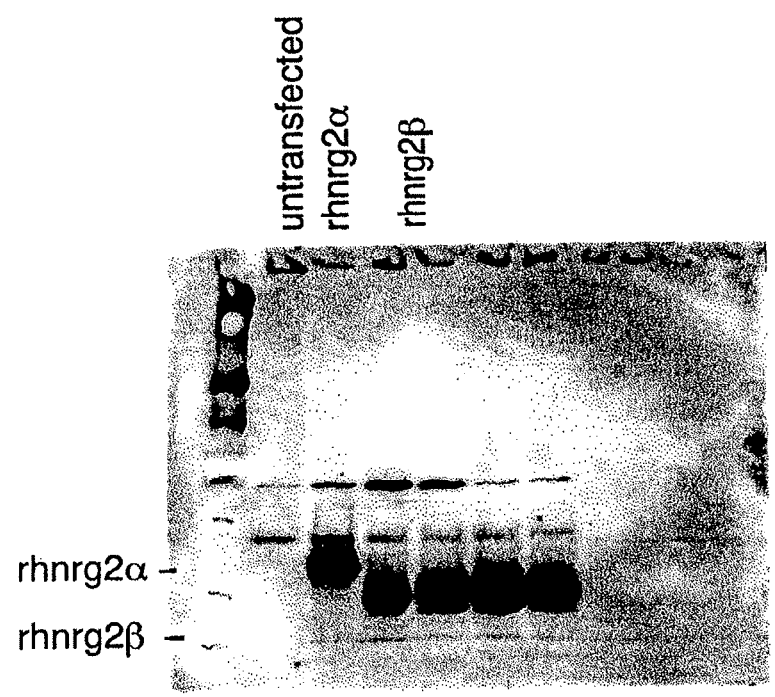
FIG. 5 shows a western blot analysis of the expression of recombinant human NRG-2α and NRG-2β.

Furthermore, analysis of culture media from transiently transfected monolayers of CHO/S cells, using the expression plasmids rhNRG-2α and rhNRG-2β and a rabbit polyclonal antibody raised against peptide K71984M, indicated that both rhNRG-2α and rhNRG-2β were expressed, and migrated at approximately 55 kD and 47 kD, respectively (FIG. 5).

Example 6

Bioassay for Assessment of Biological Activity of Expressed rhNRG-2α and rhNRG-2β

Figure 4A:
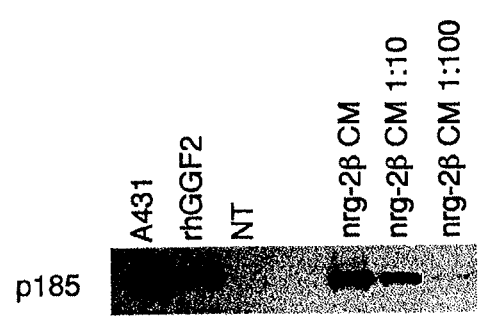
FIGS. 4A-B show western blot analyses of receptor phosphorylation on tyrosine residues in cells responsive to treatment with NRG-2 polypeptides.
Figure 4B:

A bioassay for detection of biologically-active rhNRG-2α was developed. Neuregulin signalling occurs through erbB receptor tyrosine kinases belonging to the EGF receptor family. NRG ligand binding and receptor activation can be detected by western blotting of treated cell lysates using antisera directed against phosphorylated tyrosine residues. This assay is used to study the interactions of NRG-2 proteins and erbB receptors in a variety of cell types including, but not limited to, Schwann cells, oligodendrocyte progenitors, skeletal myotubes, cardiomyocytes, and human tumor cell lines from breast and prostate adenocarcinomas. Biologically-active NRG-2 (e.g., conditioned medium from CHO cells expressing recombinant rat NRG-2β) can be detected using this assay on the human breast adenocarcinoma cell line MCF-7. The results of an experiment testing rat NRG-2β (rrNRG-2β) and rhGGF2 on MCF-7 cells by a receptor phosphotyrosine western blot is shown in FIG. 4A. MCF-7 cells were cultured in 24 well plates ($2 \times 10^5$ cell/well) and treated for 15 minutes in DMEM-0.1% FCS containing 10 ng/ml rhGGF2, or various dilutions of medium conditioned by CHO-cells expressing rhNRG-2β. Following the treatment, the media were removed and the cells were washed once, then the cultures were lysed, and samples were analyzed by western blotting (Canoll et al, Neuron 17, 229-243, 1996). Phosphorylated ErbB receptors are detected with the RC20B phosphotyrosine antibody (Transduction Laboratories, Lexington, Ky.). A positive control sample for this analysis is a lysate of A431 cells treated with EGF (left-most lane; FIG. 4A). When neither rhGGF2 nor rrNRG-2β were added to the growth media, there were no detectable proteins phosphorylated on tyrosine. However, addition of various concentrations of NRG-2β showed a dose dependent increase in phosphorylation at 185 kd. This band matched the expected position of the ErbB2 and ErbB3 receptors, which were also phosphorylated in response to treatment with rhGGF2 (10 ng/ml). Therefore, this bioassay provides a reliable method to verify the bioactivity of expressed and purified rhNRG-2α and rhNRG-2β. This assay, when applied to purified recombinant protein, enables quantification of the bioactivity of NRG-2 in dose response curves that provide comparable data to DNA synthesis assays. Receptor tyrosine kinase bioassays on MCF-7 cells treated with conditioned media from CHO/S cell transient transfections or with purified recombinant NRG proteins are also shown in FIG. 4B.

Example 7

Purification of Milligram Quantities of rhNRG-2α or β

Conditioned medium harvested from a producer cell line (expressing rhNRG-2α) is adjusted to pH 6.0 with acetic acid and loaded directly onto an S-sepharose column equilibrated with sodium acetate (pH 6.0). Bound material is eluted with 1M NaCl in acetate buffer, equilibrated in ammonium sulfate buffer and passed over a hydrophobic interaction column (Butyl Sepharose FF) in the same buffer. Bound material is eluted with low salt (800 mM ammonium sulfate) buffer and the rhNRG-2α peak collected. Collected material is buffer exchanged and concentrated to 1 mg/ml in formulation buffer (100 mM arginine, 100 mM Sodium Sulphate, 20 mM NaAc, 1% mannitol pH 6-7) using an Amicon spiral cartridge. An optional, final purification step is a Sephacryl 200 HR column and eluted rhNRG-2α peak is formulated in formulation buffer. An alternative approach is to follow the purification scheme relying on heparin affinity, Cu-chelate and C4-reversed phase chromatographies (Higashiyama et al., J. Biochem. 122: 675-680, 1997).

Proteins fractions from chromatographic columns are monitored by western blotting (e.g., see FIG. 3A-C) to identify the peak of secreted rhNRG-2α or β. Peak fractions and final preparations are analyzed by receptor phosphorylation on MCF-7 cells (see FIG. 4A-B). Purity is assessed by gel electrophoresis (coommassie blue staining) and by analytical HPLC (Vydac C8 column run in a gradient of acetonitrile in 0.1% trifluoracetic acid). Protein concentrations are determined by the bicinchoninic acid (BCA) assay (Pierce) with bovine serum albumin used as a standard.

Another general plan for purification involves capture by conventional chromatography on cation exchange followed by resolution from contaminating proteins through one or more steps, for example, by utilizing carboxymethyl Sepharose chromatography followed by reverse phase HPLC.

Briefly, carboxymethyl sepharose (fast flow) columns of varying sizes were equilibrated with 200 mM NaCl 10 mM Tris pH 7.4, then conditioned media samples were loaded, and the column was washed with approximately 3 volumes of 200 mM NaCl, 10 mM Tris pH 7.4 (until the absorbance had reached baseline). Bound protein was eluted with 500 mM NaCl, 10 Mm Tris at pH 7.4. This elution was followed by a high salt wash (1M NaCl, 10 mM Tris pH 7.4) for 3 column volumes. Fractions were collected and analyzed by western blot and gold or coommassie blue stained protein gels (4-20% acrylamide Tris-glycine-SDS). Depending on the column scale and the quantity of protein loaded captured, rhNRG-2β represented from 10-70% of the protein eluted in 0.5 M NaCl from the column. No detectable rhNRG-2β was detected in the flowthrough, nor in the 0.2 M NaCl or 1M NaCl fractions, provided that the column was not overloaded. Significant improvements in recovery were obtained (>90%) by including protease inhibitors and running the column in the cold. The scale of capture chromatography was increased, beginning with 10 ml columns, through 40 ml, 100 ml, and 200 ml columns. The overall results were consistent both in terms of recovery and purification, indicating that the scale of this step can be adjusted to suit the volume of starting material available.

Figure 7A:
FIG. 7A shows a Coomassie stained polyacrylamide gel of purified rhNRG-2β.
Figure 7B:
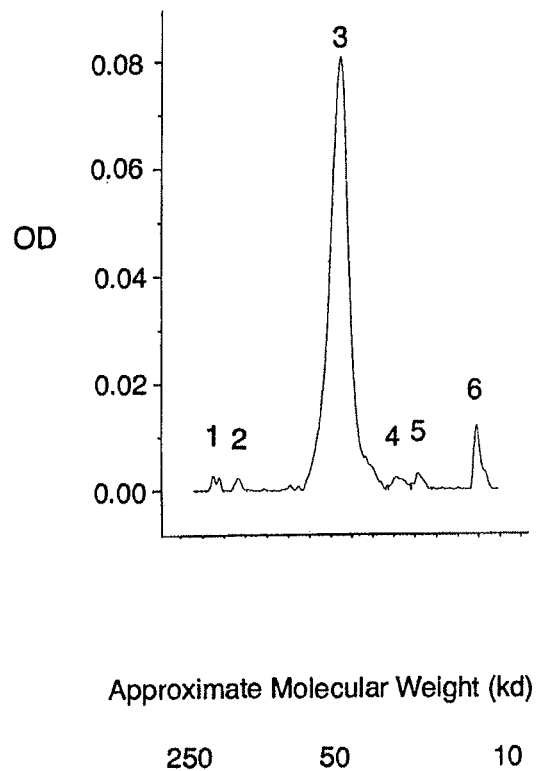
FIG. 7B shows a scan of the gel of FIG. 7A.

The purification method was further developed with reverse phase HPLC using a C4 column (Vydac 214 TP 1010, 1 cm×25 cm column) operated on a Biocad Perfusion Chromatography Workstation. A series of pilot runs were performed on pooled fractions from several carboxymethyl sepharose columns that contained rhNRG-2β in 10 mM TrisHCl pH 7.4, 0.5 M NaCl. The column was operated at a flow rate of 1 ml/min and was equilibrated in 0.2% TFA. After injecting the sample, a 10 min. column wash in 0.2% TFA was followed with a 30 min. linear ramp up to 90% acetonitrile, 0.2% TFA and a final 10 min. wash step in 90% acetonitrile, 0.2% TFA was used to complete the method. Fractions were analyzed by western blot. Only the fractions that contained very pure rhNRG-2β were included in the final pool. As assessed by coommassie blue staining of the gel shown in FIG. 7A, the preparation of rhNRG-2β was approximately 92% pure. However, approximately 60-70% of the immunoreactivity detected across the HPLC chromatograph was not included in the rhNRG-2β pool. Therefore, although 90% purification has been achieved in 2 steps, a third step may be performed to enable more complete recovery of rhNRG-2β. This third step may include heparin sepharose and/or several modifications of the reverse phase HPLC step (e.g., variations in solvents).

Figure 8:
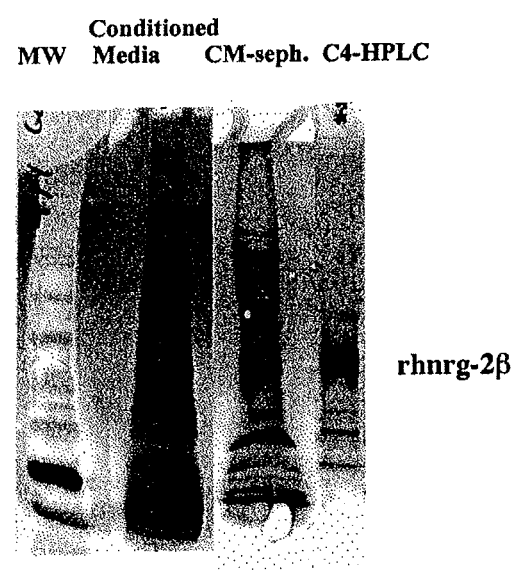
FIG. 8 shows a gold stained polyacrylamide gel of total protein and purified rhNRG-2β.

Gold staining provides another sensitive method for detecting contaminating proteins in protein preparations, and this stain readily detects nanogram quantities of protein. To visualize the purification process and to further analyze the purity of rhNRG-2β samples from different stages of purification were compared (FIG. 8). Samples were run on 4%-20% SDS PAGE (Novex, cat # EC 6025) gels in reduced conditions. The gels were transferred onto PVDF membrane, and were stained for total protein with Gold Stain (Amersham, cat # RPN490). To prevent overloading in the lane, the starting material (serum-free conditioned media) was loaded at 1% of the relative amount of the purification samples. The central observation from this analysis was that very significant purification had been achieved in two steps.

Figure 9:
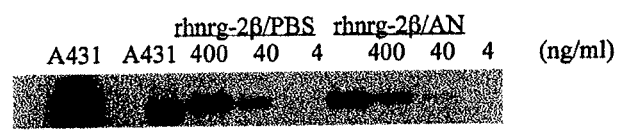
FIG. 9 shows a western blot analysis of receptor phosphorylation of tyrosine residues in cells responsive to HPLC purified rhNRG-2β.

The tyrosine phosphorylation assay performed on the MCF-7 cell line (human mammary adenocarcinoma) was used to measure the bioactivity of purified NRG-2 samples. Briefly, cultures were challenged with test samples (dilutions of purification samples in medium containing 0.1% FCS) for 15 min at 37 C, then the media was aspirated, and 50 μl 2× sample buffer containing DTT and 1 mM sodium orthovanadate was added. Samples were then prepared for electrophoresis and Western blotting. The control sample, lysate from A431 cells treated with epidermal growth factor, was provided by the vendor (Transduction Laboratories, Lexington, Ky.). In addition to monitoring rhNRG-2β production, the activity of HPLC purified samples of rhNRG-2b diluted in vehicles compatible with purification procedures such as 50% acetonitrile (AN) or PBS was examined (FIG. 9). At the concentrations used in this experiment, AN did not dramatically interfere with NRG signaling.

Example 8

NRG-2 Activities on Oligodendrocyte Progenitors

Evaluation of rhNRG-2α and rhNRG-2β effects on proliferation and survival of cultured oligodendrocyte progenitors is performed, using rhGGF2 for comparison. Oligodendrocyte progenitors are generated from 2 day old rat according to the method of McCarthy and DeVellis (*J. Cell Biol.* 85: 890-902, 1980), and the cells are cultured in N2 defined media containing 0.5% FBS (DM+) for one to three days to enrich for cells in the oligodendrocyte lineage. Purity of the cultures is established by immunofluorescence analysis using a series of antibodies directed against GFAP, a marker for astrocytes; OX42 monoclonal, a marker for microglia (Harlan Bioproducts for Science); anti-A2B5 monoclonal (Boehringer Mannheim), a marker for 0-2A progenitors; 04 and 01, which recognizes early and mature oligodendrocytes respectively (Sommer et al., *Dev. Biol* 83: 311-327, 1980); RPTP-β (gift of J. Schlessinger, NYU Med. Ctr) and nestin antibodies (Developmental Studies Hybridoma Bank) which preferentially recognize early cells in the oligodendrocyte lineage (Canoll et al., *Neuron* 17, 229-243, 1996; Gallo et al., *J. Neurosci.* 15: 394-406, 1995).

To determine the percentage of cells synthesizing DNA in response to rhNRG-2α, rhNRG-2β, or rhGGF2 cultures are treated for 16 h and for the final 4 h in the presence of 10 μM bromodeoxyuridine (BrdU; Sigma). BrdU-labelled cells are detected using fluoroscein-conjugated anti-BrdU immunodetection kit (Boehringer Mannheim). The labeling index, corresponding to the ratio of BrdU+ cells to total cells, is determined from photomicrographs of individual fields of BrdU labeled and Hoechst stained nuclei. To determine the labeling index at specific stages of differentiation, BrdU staining is combined with analysis of O4, O1 and GFAP immunofluorescence.

To assess the effect NRG-2 on cell survival, cells growing in B104 conditioned medium are changed to DM+ media for three days. They are then switched to either N2 media or DMEM with or without rhGGF2, rhNRG-2α, or rhNRG-2β for 12 or 24 hours and stained with the Live/Dead staining kit (Molecular Probes, Inc) for 15 min following the manufacturer's instructions. Morphologic criteria to quantify cell death, i.e. monitoring pyknotic cells under phase microscopy and the MTT assay (Sigma), are used in separate experiments.

Example 9

NRG-2 Activities on Olfactory Bulb Ensheathing Cells

The rat olfactory bulb is an exceptional CNS tissue. Unlike other areas of the brain, growing axons are able to enter the olfactory bulb and extend within this CNS environment throughout adult life. The glial cells of the olfactory system, known as olfactory bulb ensheathing cells (OBECs), may have an important role in CNS neural regeneration (Li et al, *J. Neurosci.* 18: 10514-10524, 1998). OBECs are unusual glial cells possessing properties of both astrocytes and Schwann cells, and may be useful cells to aid in spinal cord regeneration. OBECs express functional NRG receptors erbB2 and erbB4 (Pollock et al. *Eur. J. Neurosci.* 11: 769-780, 1999). Furthermore, high levels of NRG-2 polypeptides are expressed in the olfactory bulb. Accordingly, these OBECs are ideal candidates for comparing the bioactivities of NRG-1 to NRG-2 gene products.

OBECs are purified from postnatal day 7 rats by fluorescence activated cell sorting using the 04 antibody (Barnett, In: *Culture of Animal Cells*, I. R. Freshney, 3rd Edition. pp 337-341. Wiley-Liss, New York, N.Y., 1993; Barnett et al., *Dev Biol.* 155: 337-350, 1993). After sorting, cell suspensions are plated onto coverslips and incubated in DMEM-BS containing 10% astrocyte conditioned medium (ACM) overnight at 37° C. (to promote cell survival) before treatment with either growth factors or ACM. Mitogenic activity is assayed by incorporation of BrdU into dividing cells, and cell survival and apoptosis assays are done as described (Pollock et al. *Eur. J. Neurosci.* 11: 769-780, 1999).

Example 10

NRG-2 Activities on Mid-Brain Dopaminergic Neurons.

The NRG receptor erbB4 is expressed in midbrain dopaminergic neurons of the rat, mouse, and monkey. Delivery of recombinant human NRG proteins to the striatum is useful in the treatment of Parkinson's disease. Studies using the exemplary proteins, rhNRG-2α, rhNRG-2β, and rhGGF2 are undertaken to further investigate the response of the dopaminergic nigrastriatal system to NRGs. The two NRG proteins are compared for survival-promoting activity (i.e. protection from cell death induced by agents that induce oxidative stress) on dopaminergic neurons (for example, from both fetal rodents and human neuroblastoma cells lines, e.g., SKNNC) in vitro. Cells pre-treated with varying concentrations of rhNRG-2α, rhNRG-2β, or rhGGF2 are challenged with a twenty four hour treatment of 1 μM metadione or 100 mM diethyldithiocarbamate to induce oxidative stress, and cell death is quantified by standard methods. An in vivo model of dopamine release and electrochemical and behavioral assessments of dopaminergic function in rats can also be used.

Figure 10A:
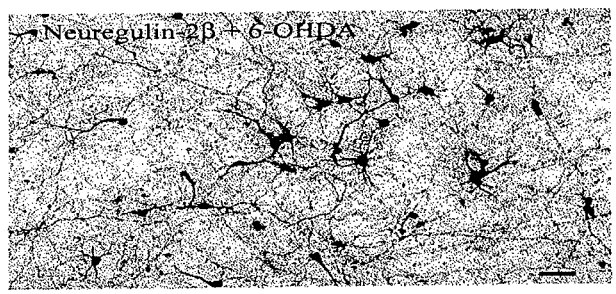
FIG. 10A shows a photograph of midbrain dopaminergic neurons pretreated with rhNRG-2β and challenged with 6-OHDA.
Figure 10B:
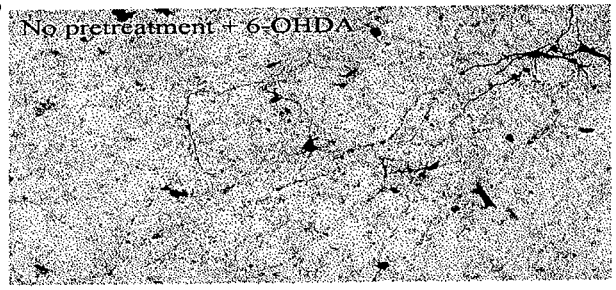
FIG. 10B shows a photograph of untreated control midbrain dopaminergic neurons challenged with 6-OHDA.

NRG proteins were tested for survival promoting activity on rat dopaminergic neurons in vitro. Specifically, it was determined if NRG proteins were neuroprotective for dopaminergic neurons that were challenged in culture with 6-hydroxydopamine (6-OHDA). Cells pre-treated with rhNRG-2β or rhGGF2 and untreated control cultures were exposed to 50 μM 6-OHDA for 24 h, then cultures were stained for tyrosine hydroxylase (TH) and examined by light microscopy (FIGS. 10A-B). FIGS. 10A-B show primary mesencephalic cultures immunostained for tyrosine hydroxylase (TH) on day in vitro (DIV) 7. The top panel shows a culture treated with 100 nanograms rhNRG-2β daily starting at DIV 0 and ending at DIV 3. On DIV 4, the culture was treated with 50 μM 6-OHDA. The bottom panel shows a culture that received no pretreatment, but was treated with 50 μM 6-OHDA on DIV 4. Both cultures were analyzed for TH immunoreactivity on DIV 7. Calibration bar equals 50 microns and applies to both top and bottom panels. Similar staining patterns were observed throughout each of the cultures. The density, number, and length of neurites of TH-positive neurons were reduced by 6-OHDA treatment in the culture receiving no pretreatment. In contrast, the culture pretreated with rhNRG-2β shows normal morphological development, which is comparable to the results observed with rhGGF2. This result has been replicated in several culture experiments. The results indicate that rhNRG-2β has beneficial effects in vivo, which can be tested, for example, in an animal model of Parkinson's disease.

Example 11

Neuronal Development and Migration in the Cerebellum

Isoforms of NRG-1, NRG-2, and the erbB4 receptor are expressed at high levels in the cerebellum (Chen et al., *J Comp Neurol* 349: 389-400, 1994; Chang et al., *Nature* 387: 509-512, 1997; Lai et al., *Neuron* 6: 691-704, 1991). RhNRG-2α, rhNRG-2β, and rhGGF2 can be evaluated in cell culture assays of migration and neurogenesis in the cerebellum. RhNRG-2α, rhNRG-2β, and rhGGF2 are compared with respect to their effect on the rate of migration of cerebellar granule neurons on a glial cell substrate. Imprint cultures of postnatal day 5 rat cerebellum containing intact Bergmann glia with migrating neurons attached to them are made as described (Anton et al., *J. Neurosci.* 16: 2283-2293, 1996). Neuronal migration is monitored using a Zeiss axiovert 135 microscope equipped with a Zeiss W63 objective, with images recorded onto an optical disk. Changes in the rate and pattern of neuronal migration, neuron-glial interactions, and morphology are monitored in response to rhNRG-2α, rhNRG-2β, and rhGGF2.

Effects on cerebellar granule neurogenesis are studied in dissociated cultures of postnatal rat cerebellar granular neurons. Dividing neural precursors are purified from postnatal day 5 cerebellum by Percoll density gradient centrifugation and placed into dissociated cell culture. Cultures are then treated with 10 μM BrdUrd (to label dividing cells) and with varying concentrations of rhNRG-2α, rhNRG-2β, and rhGGF2. After two to seven additional days in culture, differentiation into neuronal and glial cell lineages is assayed by immunostaining using cell-type specific markers, such as GFAP (glial) and TUJ1 (neuronal). For each culture condition, the total number of cells, the BrdU-labelled cells, and the cells identified with each marker are enumerated. Cells that entered a particular cell lineage since exposure to these growth factors are identified as those labelled with BrdU plus one of the markers. The percentage of BrdU-labelled cells stained with each marker thus provides a measure of the effects of each growth factor on the genesis and survival of neurons and glia. Analysis of total number of cells at various time points and the number of apoptotic cells under different conditions are used to evaluate any potential effect of rhNRG-2α, rhNRG-2β, and rhGGF2 on selective survival of neural precursors or their neuronal or glial derivatives.

Figure 12A:
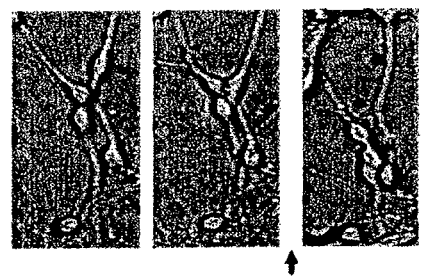
FIG. 12A shows a photograph of cerebellar granule neurons migrating on a glial cell process.
Figure 12B:
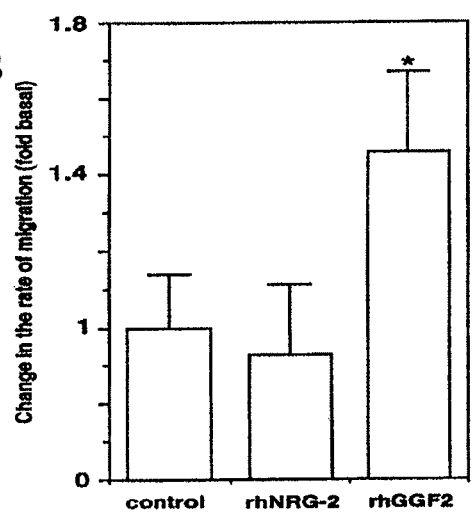
FIG. 12B shows a bar graph indicating the effect of NRG-2 on neuronal migration.

Isoforms of NRG-1, NRG-2 and the erbB4 receptor are expressed at high levels in the cerebellum, thus making in vitro studies on neural cells of the cerebellum an important component of these studies. Both rhNRG-2β and rhGGF2 were evaluated in cell culture assays of migration and neurogenesis in the cerebellum. Imprint cultures of postnatal day 5 rat cerebellum containing intact Bergmann glia with migrating neurons attached to them were made and analyzed. Neuronal migration was monitored using a Zeiss axiovert 135 microscope equipped with a Zeiss W63 objective, with images recorded onto an optical disk. Changes in the rate and pattern of neuronal migration, neuron-glial interactions, and morphology were monitored in response to rhnrg-2β and rhGGF2 (FIG. 12A-B). The rate of neuronal migration of cerebellar granule neurons was measured before and after exposure to rhNRG2β (100 ng/ml), rhGGF2 (50 ng/ml), or unsupplemented control media. FIG. 12A shows neurons migrating on a glial cell process monitored prior to (panels to the left of black arrow) and after (panels to the right of black arrow) addition of growth factors (shown here is rhGGF2). Time elapsed between each panel is one hour. FIG. 12B shows that exposure to rhGGF2 promoted the rate of migration of neurons by 45±2.1%. In contrast, neither control medium nor rhNRG-2β altered the rate of migration. The asterisk indicates significance, $P<0.05$. Data shown are mean±SEM (n>16 for each group). Therefore, in contrast to the observed increase in the rate of neuronal migration promoted by rhGGF2, rhNRG-2β had no apparent effect. However, when cerebellar neural progenitors were studied in dissociated culture, rhNRG-2β promoted external granule (EGL) neuron proliferation and/or survival (FIG. 11A-B). External granule layer (EGL) cells were dissociated and cultured in neurobasal (NB)/N2 medium or in NB/N2 medium supplemented with 100 ng/ml rhNRG-2β for 5 days. 10 μM BrdU was added to all cultures from the beginning. The cells then were fixed and probed with a polyclonal neuron-specific antibody (Tuj-1; Babco) and with anti-BrdU monoclonal antibodies. Cells that were labeled with Tuj-1 alone (i.e., neurons; asterisk[A]), BrdU+ Tuj-1 (i.e., neurons generated from dividing neuroblasts in culture; arrow [A]), and BrdU alone (i.e., non-neural cells; arrowhead[A]) were counted. Compared to the control, more neurons (arrow, [A]) were found to have incorporated BrdU (orange) in their nuclei when cultured in medium containing rhNRG-2β. BrdU immunoreactivity was detected with anti-mouse conjugated to Cy3 (Red). Tuj-1 immunoreactivity was detected with anti-rabbit conjugated to FITC. Numbers of Tuj-1 and BrdU positive cells were counted. Cell counts from the rhNRG-2β group was normalized to that from control group to obtain fold basal change in the number of BrdU positive neurons. This result suggests that rhNRG-2β promotes EGL cell proliferation or the selective survival of newly generated cerebellar granule neurons. These data therefore exemplify a bioactivity on neural cells that is more generally applicable to neuronal populations that express erbB4.

Example 12

NRG-2 Activities on Ventricular Cardiomyocytes.

To examine the role of NRG ligands and their receptors in developing and postnatal myocardium, the ability of NRG-2 proteins to promote proliferation, survival and growth of isolated neonatal and adult rat cardiac myocytes was studied. All three of the known receptors for neuregulins, erbB2, erbB3, and erbB4, are expressed in the developing heart at E14, after which erbB3 expression rapidly declines while erbB2 and erbB4 expression persists in ventricular myocytes into adulthood. The in vitro activities of rhNRG-2α and rhNRG-2β on cardiomyocytes are evaluated as compared to rhGGF2. Specifically, the two growth factors are compared for effects on cardiomyocyte survival, hypertrophy, and contractile protein expression as described below. Neonatal rat ventricular myocyte (NRVM) primary cultures are prepared as described previously (Springhorn et al., *J. Biol. Chem.* 267: 14360-14365, 1992). To selectively enrich for myocytes, dissociated cells are centrifuged twice at 500 rpm for 5 min, preplated twice for 75 min, and finally plated at low density (0.7-1×104 cells/cm2) in DME medium supplemented with 7% FBS. Cytosine arabinoside (AraC; 10M; Sigma) is added during the first 24-48 h to prevent proliferation of non-myocytes. Unless otherwise stated, all experiments are performed 36-48 h after changing to a serum-free medium, DME plus ITS (Sigma). Using this method, primary cultures with >95% myocytes are routinely obtained, as assessed by microscopic observation of spontaneous contraction and by immunofluorescence staining with a monoclonal anti-cardiac myosin heavy chain antibody (anti-MHC; Biogenesis, Sandown, N.H.).

Isolation and preparation of adult rat ventricular myocyte (ARVM) primary cultures is carried out using techniques previously described (Berger et al., *Am. J. Physiol.* 266: H341-H349, 1994). Rod-shaped cardiac myocytes are plated in culture medium on laminin-(10 (g/ml) precoated dishes for 60 min, followed by one change of medium to remove loosely attached cells. The contamination of ARVM primary cultures by non-myocytes is determined by counting with a haemocytometer and is typically less than 5%. All ARVM primary cultures are maintained in a defined medium termed "ACCITT" (Ellingsen et al., *Am. J. Physiol.* 265: H747-H754, 1993) composed of DME, supplemented with 2 mg/ml BSA, 2 mM L-carnitine, 5 mM creatine, 5 mM taurine, 0.1 (M insulin, and 10 nM triiodothyronine with 100 IU/ml penicillin and 100 (g/ml streptomycin. In experimental protocols designed to examine myocyte survival and/or apoptosis, insulin is omitted from the defined medium, which is therefore termed "ACCTT".

Measurements of rates of protein synthesis ([$^3$H]leucine uptake) are used to monitor growth factor effects on cardiomyocyte hypertrophy. For these experiments, 10 (M cytosine arabinoside is added to the culture medium. Cells are grown in serum-free medium for 36 to 48 h and then stimulated with different doses of rhNRG-2α, rhNRG-2β, or rhGGF2. After 40 h, [3H]leucine (5 (Ci/ml) is added for 8 hours, and cells washed with PBS and harvested with 10% TCA. TCA-precipitable radioactivity is determined by scintillation counting.

Immunocytochemistry is used to examine changes in myocyte phenotype with rhNRG-2α, rhNRG-2β, or rhGGF2. For example, following treatment with growth factors, cells are fixed in 4% (w/v) paraformaldehyde for 30 min at room temperature, rinsed with PBS, permeabilized with 0.1% Triton X-100 for 15 min, and then incubated with 1% FBS for another 15 min, followed by incubation with anti-myosin heavy chain (1:300) and visualized with TRITC-conjugated (NRVM) or FITC-conjugated (ARVM) second antibody. ARVM are examined using a MRC 600 confocal microscope with a Kr/Ar laser.

Figure 13:
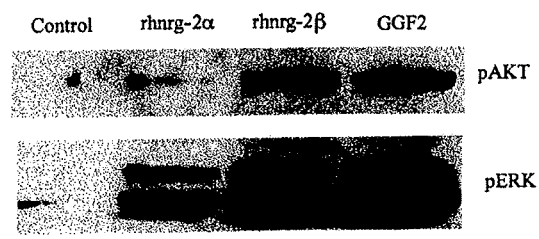
FIG. 13 shows a western blot analysis of the activation of p42/44 MAPk(Erk) and Akt by NRG-2 proteins.
Figure 14:
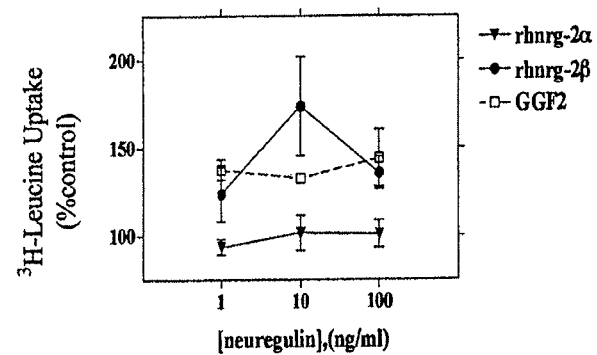
FIG. 14 shows a line graph of $^3$H-Leucine uptake into neonatal rat ventricular myocytes treated with NRG proteins.

The in vitro activities of rhNRG-2α and rhNRG-2β on cardiomyocytes as compared to rhGGF2 was evaluated. Studies on cellular hypertrophy (as monitored by measuring protein synthesis) and activation of signalling pathways including p42/44 MAPK and Akt were performed (FIG. 13 and FIG. 14). Neonatal rat ventricular myocytes isolated from 1 day old neonatal rat ventricle were plated in 24 well tissue culture plates with ~80,000 cells/well for 24 hrs in 10% FCS, then serum starved overnight. Cells were treated with recombinant neuregulins in the presence of $^3$H-leucine for 24 hrs. Cellular protein was precipitated with 5% TCA and lysed with 0.4N NaOH. $^3$H-leucine incorporation was measured with a scintillation counter, and presented as the average of 4 wells treated identically divided by the average counts in untreated cells. Neonatal rat ventricular myocytes were plated in p100s~2-3 million cells/plate for 24 hrs in 10% FCS, then serum starved 24 hrs. Cells were treated with recombinant neuregulins for 10 min, then lysed with buffer containing protease and phosphatase inhibitors (New England Biolabs). Samples representing 70 µg protein were run on 10% gel (BioRad), and transferred to PVDF membrane for detection of phophorylated Erk or Akt using New England Biolabs phospho-specific antibodies. Both rhGGF2 and rhNRG-2β increased protein synthesis by approximately 40% at all concentrations examined. However, rhNRG-2α had no effect on protein synthesis over the concentration tested. The blot shown (FIG. 13) is representative of 2 separate experiments.

These results indicate that NR2 signalling may act to promote the proliferation, survival, and growth of cardiac myocytes, both during and following myocardial trabeculation. Moreover, the persistence of NRG receptors in the postnatal and adult heart suggests a continuing role for neuregulins in the myocardial adaption to physiologic stress or injury.

Example 13

Cell Survival Assay and Detection of Apoptosis

Cell viability is determined by the 3-(4,5-dimethylthiazol-2-yl)-2,5-diphenyl tetrazolium bromide (MTT, Sigma) cell respiration assay. Primary cultures of NRVM after 2 days in serum-free medium are stimulated with different concentrations of rhNRG-2α, rhNRG-2β, or rhGGF2 for either 4 or 6 days. ARVM are maintained in ACCTT medium or ACCTT medium plus different concentrations of rhNRG-2α, rhNRG-2β, or rhGGF2 for 6 days. MTT is then incubated with the cells for 3 h at 37° C. Living cells transform the tetrazolium ring into dark blue formazan crystals that can be quantified by reading the optical density at 570 nm after cell lysis with dimethylsulfoxide.

Apoptosis is detected in neonatal and adult myocytes using the terminal deoxynucleotidyltransferase (TdT)-mediated dUTP nick end-labeling (TUNEL) assay. 3'-end labelling of DNA with fluorescein-conjugated dUTP is done using an in situ cell death detection kit (Boehringer Mannheim) following the manufacturer's instructions. Cells are counterstained with an anti-MHC antibody as described above, and the nuclei are also stained with Hoescht 33258 (10 (M, Sigma) for 5 min. More than 500 myocytes are counted in each coverslip and the percentage of TUNEL-positive myocytes is calculated.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method of increasing the cardiomyocyte survival, cardiomyocyte proliferation, cardiomyocyte growth, or cardiomyocyte differentiation in a mammal in need thereof, said method comprising administering a neuregulin 2 (NRG-2) polypeptide to said mammal in an amount effective for increasing said cardiomyocyte survival, cardiomyocyte proliferation, cardiomyocyte growth, or cardiomyocyte differentiation, wherein the NRG-2 polypeptide comprises the amino acid sequence of SEQ ID NO: 4.

2. The method of claim 1, wherein said mammal is a human.

3. The method of claim 1, wherein said mammal has a pathophysiological condition which affects cardiac muscle.

4. The method of claim 3, wherein said condition is cardiomyopathy or ischemic damage.

5. The method of claim 4, wherein said cardiomyopathy is a degenerative congenital disease.

6. The method of claim 3, wherein said condition is cardiac trauma or heart failure.

7. The method of claim 1, wherein said mammal has a pathophysiological condition which affects smooth muscle.

8. The method of claim 7, wherein said condition is selected from the group consisting of atherosclerosis, vascular lesion, vascular hypertension, and degenerative congenital vascular disease.

9. The method of claim 1, wherein said mammal is a patient with myasthenia gravis.

* * * * *

SEQUENCE LISTING

<160> NUMBER OF SEQ ID NOS: 18

<210> SEQ ID NO 1
<211> LENGTH: 994
<212> TYPE: DNA
<213> ORGANISM: Homo sapiens

<400> SEQUENCE: 1

| | | | | | |
|---|---|---|---|---|---|
| atgaggcgcg | acccggcccc | cggcttctcc | atgctgctct | tcggtgtgtc | gctcgcctgc | 60 |
| tactcgccca | gcctcaagtc | agtgcaggac | caggcgtaca | aggcacccgt | ggtggtggag | 120 |
| ggcaaggtac | aggggctggt | cccagccggc | ggctccagct | ccaacagcac | ccgagagccg | 180 |
| cccgcctcgg | gtcgggtggc | gttggtaaag | gtgctggaca | agtggccgct | ccggagcggg | 240 |
| gggctgcagc | gcgagcaggt | gatcagcgtg | ggctcctgtg | tgccgctcga | aaggaaccag | 300 |
| cgctacatct | ttttcctgga | gcccacggaa | cagcccttag | tctttaagac | ggcctttgcc | 360 |
| cccctcgata | ccaacggcaa | aaatctcaag | aaagaggtgg | gcaagatcct | gtgcactgac | 420 |
| tgcgccaccc | ggcccaagtt | gaagaagatg | aagagccaga | cgggacaggt | gggtgagaag | 480 |
| caatcgctga | agtgtgaggc | agcagccggt | aatccccagc | cttcctaccg | ttggttcaag | 540 |
| gatggcaagg | agctcaaccg | cagccgagac | attcgcatca | aatatggcaa | cggcagaaag | 600 |
| aactcacgac | tacagttcaa | caaggtgaag | gtggaggacg | ctggggagta | tgtctgcgag | 660 |
| gccgagaaca | tcctggggaa | ggacaccgtc | cggggccggc | tttacgtcaa | cagcgtgagc | 720 |
| accaccctgt | catcctggtc | ggggcacgcc | cggaagtgca | acgagacagc | caagtcctat | 780 |
| tgcgtcaatg | gaggcgtctg | ctactacatc | gagggcatca | accagctctc | ctgcaaatgt | 840 |
| ccaaatggat | tcttcggaca | gagatgtttg | gagaaactgc | ctttgcgatt | gtacatgcca | 900 |
| gatcctaagc | aaagtgtcct | gtgggataca | ccggggacag | gtgtcagcag | ttcgcaatgg | 960 |
| tcaacttctc | caagcacctt | ggatttgaat | taaa | | | 994 |

<210> SEQ ID NO 2
<211> LENGTH: 330
<212> TYPE: PRT
<213> ORGANISM: Homo sapiens

<400> SEQUENCE: 2

Met Arg Arg Asp Pro Ala Pro Gly Phe Ser Met Leu Leu Phe Gly Val
1               5                   10                  15

Ser Leu Ala Cys Tyr Ser Pro Ser Leu Lys Ser Val Gln Asp Gln Ala
            20                  25                  30

Tyr Lys Ala Pro Val Val Val Glu Gly Lys Val Gln Gly Leu Val Pro
        35                  40                  45

Ala Gly Gly Ser Ser Ser Asn Ser Thr Arg Glu Pro Pro Ala Ser Gly
    50                  55                  60

Arg Val Ala Leu Val Lys Val Leu Asp Lys Trp Pro Leu Arg Ser Gly
65                  70                  75                  80

Gly Leu Gln Arg Glu Gln Val Ile Ser Val Gly Ser Cys Val Pro Leu
                85                  90                  95

```
Glu Arg Asn Gln Arg Tyr Ile Phe Phe Leu Glu Pro Thr Glu Gln Pro
                100                 105                 110

Leu Val Phe Lys Thr Ala Phe Ala Pro Leu Asp Thr Asn Gly Lys Asn
            115                 120                 125

Leu Lys Lys Glu Val Gly Lys Ile Leu Cys Thr Asp Cys Ala Thr Arg
        130                 135                 140

Pro Lys Leu Lys Lys Met Lys Ser Gln Thr Gly Gln Val Gly Glu Lys
145                 150                 155                 160

Gln Ser Leu Lys Cys Glu Ala Ala Gly Asn Pro Gln Pro Ser Tyr
                165                 170                 175

Arg Trp Phe Lys Asp Gly Lys Glu Leu Asn Arg Ser Arg Asp Ile Arg
            180                 185                 190

Ile Lys Tyr Gly Asn Gly Arg Lys Asn Ser Arg Leu Gln Phe Asn Lys
        195                 200                 205

Val Lys Val Glu Asp Ala Gly Glu Tyr Val Cys Glu Ala Glu Asn Ile
    210                 215                 220

Leu Gly Lys Asp Thr Val Arg Gly Arg Leu Tyr Val Asn Ser Val Ser
225                 230                 235                 240

Thr Thr Leu Ser Ser Trp Ser Gly His Ala Arg Lys Cys Asn Glu Thr
                245                 250                 255

Ala Lys Ser Tyr Cys Val Asn Gly Gly Val Cys Tyr Tyr Ile Glu Gly
            260                 265                 270

Ile Asn Gln Leu Ser Cys Lys Cys Pro Asn Gly Phe Phe Gly Gln Arg
        275                 280                 285

Cys Leu Glu Lys Leu Pro Leu Arg Leu Tyr Met Pro Asp Pro Lys Gln
    290                 295                 300

Ser Val Leu Trp Asp Thr Pro Gly Thr Gly Val Ser Ser Ser Gln Trp
305                 310                 315                 320

Ser Thr Ser Pro Ser Thr Leu Asp Leu Asn
                325                 330

<210> SEQ ID NO 3
<211> LENGTH: 897
<212> TYPE: DNA
<213> ORGANISM: Homo sapiens

<400> SEQUENCE: 3
atgaggcgcg acccggcccc cggcttctcc atgctgctct tcggtgtgtc gctcgcctgc    60
tactcgccca gcctcaagtc agtgcaggac caggcgtaca aggcacccgt ggtggtggag   120
ggcaaggtac aggggctggt cccagccggc ggctccagct ccaacagcac ccgagagccg   180
cccgcctcgg tcgggtggc gttggtaaag gtgctggaca agtggccgct ccggagcggg   240
gggctgcagc gcgagcaggt gatcagcgtg gctcctgtg tgccgctcga aggaaccag    300 cgctacatct ttttcctgga gcccacggaa cagcccttag tctttaagac ggcctttgcc   360
cccctcgata ccaacggcaa aaatctcaag aaagaggtgg gcaagatcct gtgcactgac   420
tgcgccaccc ggcccaagtt gaagaagatg aagagccaga cgggacaggt gggtgagaag   480
caatcgctga gtgtgaggc agcagccggt aatccccagc cttcctaccg ttggttcaag   540
gatggcaagg agctcaaccg cagccgagac attcgcatca aatatggcaa cggcagaaag   600
aactcacgac tacagttcaa caaggtgaag gtggaggacg ctggggagta tgtctgcgag   660
gccgagaaca tcctggggaa ggacaccgtc cggggccggc tttacgtcaa cagcgtgagc   720
accaccctgt catcctggtc ggggcacgcc cggaagtgca acgagacagc caagtcctat   780
```

```
tgcgtcaatg gaggcgtctg ctactacatc gagggcatca accagctctc ctgcaagtgt    840
cctgtgggat acaccgggga caggtgtcag cagttcgcaa tggtcaactt ctcctaa       897
```

<210> SEQ ID NO 4
<211> LENGTH: 298
<212> TYPE: PRT
<213> ORGANISM: Homo sapiens

<400> SEQUENCE: 4

| Met | Arg | Arg | Asp | Pro | Ala | Pro | Gly | Phe | Ser | Met | Leu | Leu | Phe | Gly | Val |
|---|---|---|---|---|---|---|---|---|---|---|---|---|---|---|---|
| 1 | | | | 5 | | | | | 10 | | | | | 15 | |

Ser Leu Ala Cys Tyr Ser Pro Ser Leu Lys Ser Val Gln Asp Gln Ala
            20                  25                  30

Tyr Lys Ala Pro Val Val Val Glu Gly Lys Val Gln Gly Leu Val Pro
                35                  40                  45

Ala Gly Gly Ser Ser Ser Asn Ser Thr Arg Glu Pro Pro Ala Ser Gly
     50                  55                  60

Arg Val Ala Leu Val Lys Val Leu Asp Lys Trp Pro Leu Arg Ser Gly
65                  70                  75                  80

Gly Leu Gln Arg Glu Gln Val Ile Ser Val Gly Ser Cys Val Pro Leu
                85                  90                  95

Glu Arg Asn Gln Arg Tyr Ile Phe Phe Leu Glu Pro Thr Glu Gln Pro
            100                 105                 110

Leu Val Phe Lys Thr Ala Phe Ala Pro Leu Asp Thr Asn Gly Lys Asn
        115                 120                 125

Leu Lys Lys Glu Val Gly Lys Ile Leu Cys Thr Asp Cys Ala Thr Arg
    130                 135                 140

Pro Lys Leu Lys Lys Met Lys Ser Gln Thr Gly Gln Val Gly Glu Lys
145                 150                 155                 160

Gln Ser Leu Lys Cys Glu Ala Ala Gly Asn Pro Gln Pro Ser Tyr
                165                 170                 175

Arg Trp Phe Lys Asp Gly Lys Glu Leu Asn Arg Ser Arg Asp Ile Arg
            180                 185                 190

Ile Lys Tyr Gly Asn Gly Arg Lys Asn Ser Arg Leu Gln Phe Asn Lys
        195                 200                 205

Val Lys Val Glu Asp Ala Gly Glu Tyr Val Cys Glu Ala Glu Asn Ile
    210                 215                 220

Leu Gly Lys Asp Thr Val Arg Gly Arg Leu Tyr Val Asn Ser Val Ser
225                 230                 235                 240

Thr Thr Leu Ser Ser Trp Ser Gly His Ala Arg Lys Cys Asn Glu Thr
                245                 250                 255

Ala Lys Ser Tyr Cys Val Asn Gly Gly Val Cys Tyr Tyr Ile Glu Gly
            260                 265                 270

Ile Asn Gln Leu Ser Cys Lys Cys Pro Val Gly Tyr Thr Gly Asp Arg
        275                 280                 285

Cys Gln Gln Phe Ala Met Val Asn Phe Ser
    290                 295

<210> SEQ ID NO 5
<211> LENGTH: 20
<212> TYPE: DNA
<213> ORGANISM: Homo sapiens

<400> SEQUENCE: 5

```
gcatcaacca gctctcctgc                                                 20
```

```
<210> SEQ ID NO 6
<211> LENGTH: 20
<212> TYPE: DNA
<213> ORGANISM: Homo sapiens

<400> SEQUENCE: 6
gcatcaacca gctctcctgc                                              20

<210> SEQ ID NO 7
<211> LENGTH: 20
<212> TYPE: DNA
<213> ORGANISM: Homo sapiens

<400> SEQUENCE: 7
tgcgaactgc tgacacctgt                                              20

<210> SEQ ID NO 8
<211> LENGTH: 21
<212> TYPE: DNA
<213> ORGANISM: Homo sapiens

<400> SEQUENCE: 8
ccaccttttg agcaagttca g                                            21

<210> SEQ ID NO 9
<211> LENGTH: 21
<212> TYPE: DNA
<213> ORGANISM: Homo sapiens

<400> SEQUENCE: 9
gaggtggctt atgagttctt c                                            21

<210> SEQ ID NO 10
<211> LENGTH: 19
<212> TYPE: DNA
<213> ORGANISM: Homo sapiens

<400> SEQUENCE: 10
ggccaccaca cagacgatg                                               19

<210> SEQ ID NO 11
<211> LENGTH: 20
<212> TYPE: DNA
<213> ORGANISM: Homo sapiens

<400> SEQUENCE: 11
gtgagcacca ccctgtcatc                                              20

<210> SEQ ID NO 12
<211> LENGTH: 34
<212> TYPE: DNA
<213> ORGANISM: Homo sapiens

<400> SEQUENCE: 12
gagctagtct agagtggctt atgagtattt cttc                              34

<210> SEQ ID NO 13
<211> LENGTH: 35
<212> TYPE: DNA
<213> ORGANISM: Homo sapiens

<400> SEQUENCE: 13
cagcagttcg caatggtcaa cttctcctaa gcacc                             35
```

```
<210> SEQ ID NO 14
<211> LENGTH: 34
<212> TYPE: DNA
<213> ORGANISM: Homo sapiens

<400> SEQUENCE: 14
cagcagttcg caatggtcaa cttctccaag cacc                                 34

<210> SEQ ID NO 15
<211> LENGTH: 35
<212> TYPE: DNA
<213> ORGANISM: Homo sapiens

<400> SEQUENCE: 15
cagcagttcg caatggtcaa cttctcctaa gcacc                                35

<210> SEQ ID NO 16
<211> LENGTH: 23
<212> TYPE: PRT
<213> ORGANISM: Artificial Sequence
<220> FEATURE:
<223> OTHER INFORMATION: derived from Rattus norvegicus and Homo sapiens

<400> SEQUENCE: 16

Ala Pro Leu Glu Arg Asn Gln Arg Tyr Ile Phe Phe Leu Glu Pro Thr
1               5                   10                  15

Glu Gln Pro Leu Val Phe Lys
            20

<210> SEQ ID NO 17
<211> LENGTH: 17
<212> TYPE: PRT
<213> ORGANISM: Artificial Sequence
<220> FEATURE:
<223> OTHER INFORMATION: derived from Rattus norvegicus and Homo sapiens

<400> SEQUENCE: 17

Asn Ser Arg Leu Gln Phe Asn Lys Val Lys Val Glu Asp Ala Gly Glu
1               5                   10                  15

Tyr

<210> SEQ ID NO 18
<211> LENGTH: 15
<212> TYPE: PRT
<213> ORGANISM: Artificial Sequence
<220> FEATURE:
<223> OTHER INFORMATION: derived from Rattus norvegicus and Homo sapiens

<400> SEQUENCE: 18

Asn Gly Gly Val Cys Tyr Tyr Ile Glu Gly Ile Asn Gln Leu Ser
1               5                   10                  15
```